United States Patent [19]
Ichikawa et al.

[11] Patent Number: 5,804,415
[45] Date of Patent: Sep. 8, 1998

[54] PROSTAGLANDIN E RECEPTORS, THEIR DNA AND PRODUCTION

[75] Inventors: Atsushi Ichikawa, Besshohonmachi; Shuh Narumiya, Kyoto, both of Japan

[73] Assignee: Takeda Chemical Industries, Ltd., Osaka, Japan

[21] Appl. No.: 685,945

[22] Filed: Jul. 22, 1996

Related U.S. Application Data

[62] Division of Ser. No. 390,162, Feb. 17, 1995, Pat. No. 5,576,192, which is a continuation of Ser. No. 24,179, Feb. 23, 1993, abandoned.

[30] Foreign Application Priority Data

Feb. 24, 1992 [JP] Japan .................................... 4-036580
Mar. 23, 1992 [JP] Japan .................................... 4-064889

[51] Int. Cl.$^6$ ........................... C12N 15/12; C07K 14/705
[52] U.S. Cl. .................. 435/69.1; 536/23.5; 435/252.3; 435/254.11; 435/320.1; 435/325
[58] Field of Search ...................... 536/23.5; 435/69.1, 435/325, 320.1, 252.3, 254.11

[56] References Cited

PUBLICATIONS

Sugimoto et al., J. Biol. Chem., 268, 2712–2718, 1993, Feb. 5, 1993.
Yukihiko Sugimoto et al., Cloning and Expression of a cDNA for Mouse Prostaglandin E Receptor EP$_3$ Subtype, The Journal of Biological Chemistry, vol. 267, No. 10, pp. 6463–6466 (Apr. 5, 1992).
Masakazu Hirata et al., Cloning and expression of cDNA for a human thromboxane A$_2$ receptor, Nature, vol. 349, pp. 617–620 (Feb. 14, 1991).
Wolfgang Holter et al., Expression of GTP–binding proteins . . . Chemical Abstract, vol. 115, No. 1, Abstract No. 6785z (Jul. 8, 1991).
Tsuyoshi Watanabe et al., Characterization of partially purified . . . Chemical Abstract, vol. 115, No. 17, Abstract No. 177670n (Oct. 28, 1991).
Shigeo Suzuki et al., Prostaglandin E2 receptor and GTP binding . . . Chemical Abstract, vol. III, No. 21, Abstract No. 192618n (Nov. 20, 1989).
Dong et al., Br. J. Pharmac., vol. 87, 97–107, 1986.
Halushka et al., Annu. Rev. Pharm. Tox., vol. 10, 213–239, 1989.
Jacobs et al., Nature, vol. 313, 806–810, 1985.
Lopaschuk et al., Circulation Research, vol. 65(3), 538–545, 1989.
Sugimoto et al., J. Biol. Chem., vol. 267(10), 6463–6466, 1992.
Coleman et al., Prostanoids and their Receptors, Comprehensive Medicinal Chemistry, vol. 3, pp. 643, 1989.
Hirata et al., Nature, vol. 349, pp. 617, 1991.
Libert et al., Science, vol. 244, pp. 569, 1989.
Masu et al., Nature, vol. 329, pp. 836, 1987.
Sugimoto et al., Journal of Biol. Chem., vol. 268, 2712–2718, 1993.

*Primary Examiner*—Sally P. Teng
*Attorney, Agent, or Firm*—Finnegan, Henderson, Farabow, Garrett & Dunner, L.L.P.

[57] ABSTRACT

Disclosed are (1) a protein capable of receiving PGE, (2) a recombinant DNA coding for said protein, (3) a vector having said DNA, (4) a transformant carrying said vector, and (5) a method for producing said protein wherein said transformant is cultured in a culture medium, the protein being useful not only in cloning other PGE receptor genes, clarifying the structure of PGE receptors and elucidating the function of PGE, but also in searching for PGE antagonists and agonists and so on.

6 Claims, 11 Drawing Sheets

FIG. 1A

```
                   VII
     C  N  S  F  L  I  A  V  R  L  A  S  L  N  Q  I  L  D  P  W  V  Y  L  L  L     325
301  TGCAATTCCTTTCTAATTGCAGTTCGCCTGGCTTCGCCTGAACCAGATCTTGGATCCCTGGGTTTATCTGCTGCTA    975

R  K  I  L  L  R  K  F  C  Q  I  R  D  H  T  N  Y  A  S  S  T  S  L  P        350
326  AGAAAGATCCTTCTTCGGAAGTTCTGCCAGATCAGAGACCACACCAACTATGCTTCCAGCTCCACCTCCCTTGCCC   1050

C  P  G  S  A  L  M  W  S  D  Q  L  E  R                                       365
351  TGCCCAGGCTCCCTCAGCCCTGATGTGGAGTGACCAGCTGGAAAGATGATGAACAACCTGAAGTGGACTTTCATTG   1125

1126 CAGTACCTGTTCCCTGGGTCTCTGAGAATTTCTTCCCCAGGAAGGATGACTGAGTATTTGGATTGTATCTTCT      1200
1201 TTTGGCCTCAATTTTAAGTTTCCTTGCCATTAAACACACTGCACTTTGTGACAACTCTCAGAACTCTCCAGCTG    1275
1276 GTTGTTAGCTGTCCTGTTCCTGTGAAGACTTGAGACTTCCAGCCTCCTCCAGAACCTTCAGAACTTTGAGAGTCTG  1350
1351 GAGACTCAGTGCAGATAGGTTCAGAGAATATCTCCAGAAGCAGCATAAGTCACATGAAGCATCAATGTGTTGAC    1425
1426 TCTTCTAAATAAGCCATGAGCCAAGACAAGAGTCTACATGAGAGCCAAGATTCTGCAAAGGGTATTGTTCA        1500
1500 TCTAAGAAGGTATACACAGAGAATCGTGTGTCCTATCATTCCCTGCTTTAAAGGGAGAAGTTTAGCTAAAGACACA  1575
1576 CCAAGAAGGTATACACAGAGAATCGTGTGTCCTATCATTCCCTGCTTTAAAGGGAGAAGTTTAGCTAAAGACACA   1650
1651 ACTGGCTCCTCAGTAATTCAGGAATTCCAAAGCTAGTGACTAAATGTTCAGCTAGAGTTCTCATTAAGACACA     1725
1726 TTCCAGGTGTCACTCAGTTCCAAAGCTATTTTTGAATTTTGAATTTCTCATAATTGTGCTCAGCGAGCA         1800
1801 ATTATCATTCATTCCAGTCCAATGCTATTTTTGAATTTTGAATTACTATCTTCTCATAATTGTGCTCAGCAGCA    1875
1876 CAATAAAAAGGGGGGGCAAATTACTAAGTGACAGTTATCTTAGTCTAAGTAAAATAAAAAAAAAAAAAAAAAAAA   1950
1951 AATGATTTTGTCTGTGTTGAACTTTTTTATGAAATAA                                          1989
```

```
                 I  R  D  H  T  N  Y  A  S  S  S  T  S  L  P  C  P  G  S  S  A  L  M  W  S
      (MP660)   ATCAGAGACCACACCAACTATGCTTCCAGTGCTTCCACCTCCTTGCCCTGCCCAGGCTCCTCAGCGCTCCTGATGTGGAGT     1005
                                                 peptide-α                                            335

991  CGGAAGTTCTGCCAG---------------------------------------------------------------------------
 331   R  K  F  C  Q

D  Q  L  E  R  •
      GACCAGCTGGAAAG
                  89

ATGATGAACAACCTGAAGTGGACTTTCATTGCAGTACCTGTTTCCCTGGGTCTGAGAATTTCTCCCAGGGAA   1080
                                                                 M  M  N  N  L  K  W  T  F  I  A  V  P  V  S  L  G  L  R  I  S  G  P  R  E    360
1006                                                                             peptide-β
336

1081                                                                                                  GGATGACTGAGTATTTTGGATTGTATCTTCTTTTGGCCTCAATTTTAAGTTTTCCTGCCATTAAACACACCGAGACAAGCTTTCTTAGG  1170
361                                                                                                    G  •                                                                                                361

1171  ATAATCTGAGAGTCTCTGGTTGTTAGCTGTGTTCCTGTGAAGACTCTGCACTTGAGACGGGGGCAAGAGACGACACAGAGCAGCATGG   1260
1261  AGAGACTCAGTGCAGAAATATCTCCAGCCTCAGAACCTTT......
```

```
                                                                                           960
GACTTTCCGCCGCGCAGGAGTTTCGGGCGCATCGCGGGCATCGCGGGCGTCCGGAGATCGTCATCTACTGCTCATTCCGCTGCGAGTG
 D  F  R  R  R  S  F  R  R  I  A  G  A  E  I  Q  M  V  I  L  L  I  A  T  S  L  V  V  L  I  C  S  I  P  L  V  V  R  V    320
  ★         ★                                        VI
                                                                                          1080
TTCATTAACCAGTTATATCAGCCAAACTGTTGGTGAAAGACATCAGCAGAAACCCAGATTTGCAGGCCATCAGATTCGTTCTTGAACCCATCCTGGATTTACATCCTTCTT
 F  I  N  Q  L  Y  Q  P  N  V  V  K  D  I  S  R  N  P  D  L  Q  A  I  R  I  A  S  V  N  P  I  L  D  P  W  I  Y  I  L  L    360
                                                                  VII
                                                                                          1200
CGGAAGACTGTGCTCAGTAAAGCCATAGAGAAGATCAAGTGCCTCTTCTGCCGCATTGGCGGTTCCGGCAGAGACAGTCGGCCCAGCACTCGGCGAGACATCTTCCGCC
 R  K  T  V  L  S  K  A  I  E  K  I  K  C  L  F  C  R  I  G  G  S  G  R  D  S  S  A  Q  H  C  S  E  S  R  R  T  S  S  A    400
                                                                                    ★
                                                                                    ★
                                                                                          1320
ATGTCCGGCCACTCTCGCTCCTTCCTCGCCCGGGAGTTAAAGGAGATCAGCAGCACCCCTCTGTACCTTCTGCCAGACCTGACTGAAAGCAGCTCGAGGCCAGGAATTTGCTT
 M  S  G  H  S  R  S  F  L  A  R  E  L  K  E  I  S  S  T  S  Q  T  L  L  Y  L  P  D  L  T  E  S  S  L  G  G  R  N  L  L    440
                                                                                          1440
CCAGGTTGGCATGGGCATGGGCCTGACCCAAGCAGACCCAAGACTTCCCTCCCTCCCAGGCCAGGACTCTGAGAGTGTCCTCTTGGTGAT
 P  G  S  H  G  M  G  L  T  Q  A  D  T  T  S  L  R  T  L  R  I  S  E  T  S  D  S  S  Q  G  Q  D  S  E  S  V  L  L  V  D    480
                                                                                          1560
GAGGTTAGTGGGAGCCACAGAGAGGAGCCTGCCTCTAAAGGAAACTCTCTGCAAGTCACATTCCCAGTGAAATTATCTGAAAACTCTGAAATTATCTGAAAATGTATATAGTAGCTAAAGGGGAATCT
 E  V  S  G  S  H  R  E  E  P  A  S  K  G  N  S  L  Q  V  T  F  P  S  E  T  L  K  L  S  E  K  C  I                          513
                                                                                          1680
TATAAATCCTGTGCAATAGACATACAGCTGTATACTCAGAAGGGCTGTCTTCATCTGACTCTCCACTAGAGAACAGGCGAGCTCCTGAGGCTCCTCAAGGCTGCAGACTGAGGTCCTT
                                                                                          1800
GAGTGCCAGGCTTGAAGCACATTGGCTGTCATTCTGATGTGACTCGAGATTGCAGTTGCAACTTGGCAGCTTTTTTTCTGACAGGAAGATGGCAGAAGCTACGCTATTGTCATAGC
                                                                                          1920
AAAAGAGCTTTCTATTTGGCACATACCAGGGGTCCAGCTGGTCCTGAGGACTGAGGGCTCAGTCTGAGGACTACCTTACAGCTGAGGACTACTTAAGCATGAAATGTGAATTT
                                                                                          2040
TTATTGTTGGAAATAATAATTAAGTTATTATTGTTCTTTCTCGTGAGAAGTTTATTGTTAATACAAGTGAAATACACATGATATGCCCTCCTGCCAATATAACCAGCTAATATT
                                                                                          2160
GTCGATGTTATTTTTTTTTCCATAAACAAGTTCAGGCCAAAGTGTTGAAAACAGAGTGAAACTAATATCTATAAAATCTATAAAATTTTAAAATAGTTTAGTATCATCAAAGAAAA
                                                                                          2280
AATAGTAGTATTTAAGATGTGAAAAATGAACAACCTAAAATATATTTTCCAAGCTATATATATAATAATGAAAAATAAAAACATTACATTTATTTATTCCAGAAAACTGTGATTTTAGGATT
                                                                                          2309
ACCTAACATTGCTCGGTAAATATTTTCAAC

FIG. 6B
```

PROSTAGLANDIN E RECEPTORS, THEIR DNA AND PRODUCTION

This is a division of application Ser. No. 08/390,162, filed Feb. 17, 1995, U.S. Pat. No. 5,576,192, a continuation of application Ser. No. 08/024,179, filed Feb. 23, 1993, now abandoned.

FIELD OF THE INVENTION

This invention relates to a PGE (especially $PGE_2$) receptor which binds to prostaglandin (PG) E, particularly prostaglandin $E_2$ ($PGE_2$), which is known to be involved widely in digestive tract constriction and relaxation, gastric acid and intestinal juice secretion, smooth muscle relaxation, neurotransmitter release and other phenomena in vivo, on the cell membrane, and transmits information on $PGE_2$ etc. to cells, and a gene which codes therefor.

BACKGROUND OF THE INVENTION

The importance of PGE, particularly $PGE_2$, in vivo is widely recognized. Analyses of the physiological and pharmacological action of $PGE_2$ and action sites have suggested that there exist at least three types of PGE receptors, $EP_1$, $EP_2$ and $EP_3$ and they are thought to be different in their signal transduction. These subtypes are presumed coupled to stimulation of phospholipase C, and stimulation and inhibition of adenylate cyclase, respectively. (R. A. Coleman, I. Kennedy, P. P. A. Humphrey, K. Bunce and P. Lumley, Comprehensive Medicinal Chemistry, ed. C. Hansch, P. G. Sammes and J. B. Taylor, Vol. 3, pp. 643–714, Pergamon Press, 1990 and Annu. Rev. Pharm. Tox. 10, 213–239 (1989)). Among PGE receptor subtypes, the $EP_2$ receptor has been suggested to be involved in relaxation in trachea (Br. J. Pharmacol. 87, 45 (1986)) and ileum circular muscle (Br. J. Pharmacol. 105, 271–278 (1992)), vasodilatation in various blood vessels, and stimulation of sodium and water reabsorption in kidney tubulus (J. Clin. Invest. 47, 1154–1161 (1968) and J. Biol. Chem. 263, 6155–6160 (1988)). One of the most important functions of $PGE_2$ through $EP_2$ receptor has been proposed to be negative regulation of immune system (Am. Rev. Respir. Dis. 135, 72–77 (1987)) and inflammation, and the $EP_3$ receptor has been suggested to be involved in such $PGE_2$ actions as inhibition of gastric acid secretion (Chen et al., 1988. Gastroenterology 94, 1121–1129), modulation of neurotransmitter release (Hedqvist et al., 1972. Neuropharmacology 11, 177–187; Ohia and Jumblatt, 1990. J. Pharmacol. Exp. Ther. 255, 11–16), inhibition of lipolysis in adipose tissue (Richelsen et al., 1984. J. Lipid Res. 26, 127–134), and inhibition of sodium and water reabsorption in kidney tubulus (Garcia-Perez et al., 1984. J. Clin. Invest. 74, 63–74). However, no $PGE_2$ receptor genes have been successfully cloned; their distribution, structure and function remain to be investigated. There has been urgent demand for their elucidation for the purpose of clarifying PGE-associated, particularly $PGE_2$-associated diseases, and for developing effective pharmaceuticals for such diseases.

OBJECT OF THE INVENTION

As stated above, the nature of the PGE receptor remains largely unknown. However, if a gene which codes for at least one type thereof is successfully cloned to yield a transformant which constantly expresses the PGE receptor, cloning of the genes of other types of PGE receptor and structural determination of the PGE receptor will be feasible, but also the role of PGE, particularly $PGE_2$ in vivo will be clarified.

It is also expected that receptor-specific antibodies will be successfully obtained by using a transformant which expresses the receptor as an immunogen, which will contribute to elucidation of the histologic distribution of receptor-expressing cells.

Generally, prostaglandin (PG) receptors are thought to be highly homologous to each other with respect to the amino acid sequence of the ligand-binding site. It is therefore conjectured that part of the DNA sequence of the human thromboxane (TX) $A_2$ receptor gene [M. Hirata et al., Nature, 349, 617 (1991)] is very similar to the DNA sequence of the gene of the receptor of PGE such as $PGE_2$. Based on this idea, the present inventors succeeded in cloning from mouse cells a gene which codes for the $EP_3$ receptor, a subtype of mouse $PGE_2$ receptor, by using part of the human $TXA_2$ receptor gene as a probe, and further in cloning from mouse cells a gene which codes for the $EP_2$ receptor, a subtype of mouse $PGE_2$ receptor, by using part of the mouse $EP_3$ receptor gene as a probe. The present inventors constructed their recombinant DNA containing each of said genes, and then found that the transformants resulting from transformation with each of said DNAs, whether entirely or partially, is capable of binding to $PGE_2$.

The present inventors made further investigations based on these findings, and developed the present invention.

SUMMARY OF THE INVENTION

An object of the present invention is to provide (1) a protein capable of receiving PGE, (2) a recombinant DNA containing a gene which codes for the protein of (1) above, (3) a vector containing the recombinant DNA of (2) above, (4) a transformant carrying the vector of (3) above, and (5) a method of producing the protein of (1) above wherein the transformant of (4) above is cultured.

BRIEF DESCRIPTION OF THE DRAWINGS

FIG. 1 shows the base sequence of the clone MP660 containing the gene which codes for the $PGE_2$ receptor, and the amino acid sequence deduced therefrom. The figure includes DNA sequence SEQ ID NO:1 and amino acid sequence SEQ ID NO:2.

FIG. 4 shows the base sequence of the clone MP653 containing the gene which codes for the $PGE_2$ receptor, and the amino acid sequence deduced therefrom. The figure includes DNA sequence SEQ ID NO:3 and amino acid sequence SEQ ID NO:4. The boxed portion of FIG. 4 designated "peptide-α" is present only in MP 660, and is included in FIG. 4 for comparison with MP653.

FIG. 6 shows the base sequence of the clone MP412 containing the gene which codes for the $PGE_2$ receptor, and the amino acid sequence deduced therefrom. The figure includes DNA sequence SEQ ID NO:5 and amino acid sequence SEQ ID NO:6.

DESCRIPTION OF THE PREFERRED EMBODIMENT

PGEs for the present invention include PGE$_1$ and PGE$_2$, with preference given to PGE$_2$. The capability of receiving PGE$_2$ means that the receptor is capable of specifically binding to PGE$_2$ or a similar substance in the transmembrane domain, and that the structural change due to such ligand binding induces activation of related GTP-binding protein in the intracellular domain.

The protein of the present invention, which is capable of receiving PGE (hereinafter also referred to as PGE receptor), is preferably a protein which is capable of receiving PGE$_2$ (hereinafter also referred to as PGE$_2$ receptor), and may be of several types, including human, chicken and mouse, and may be a glycoprotein resulting from sugar chain binding to the sugar-binding site or a complex protein such as phosphoprotein resulting from phosphorylation at the phosphorylation site.

Figure 1A:
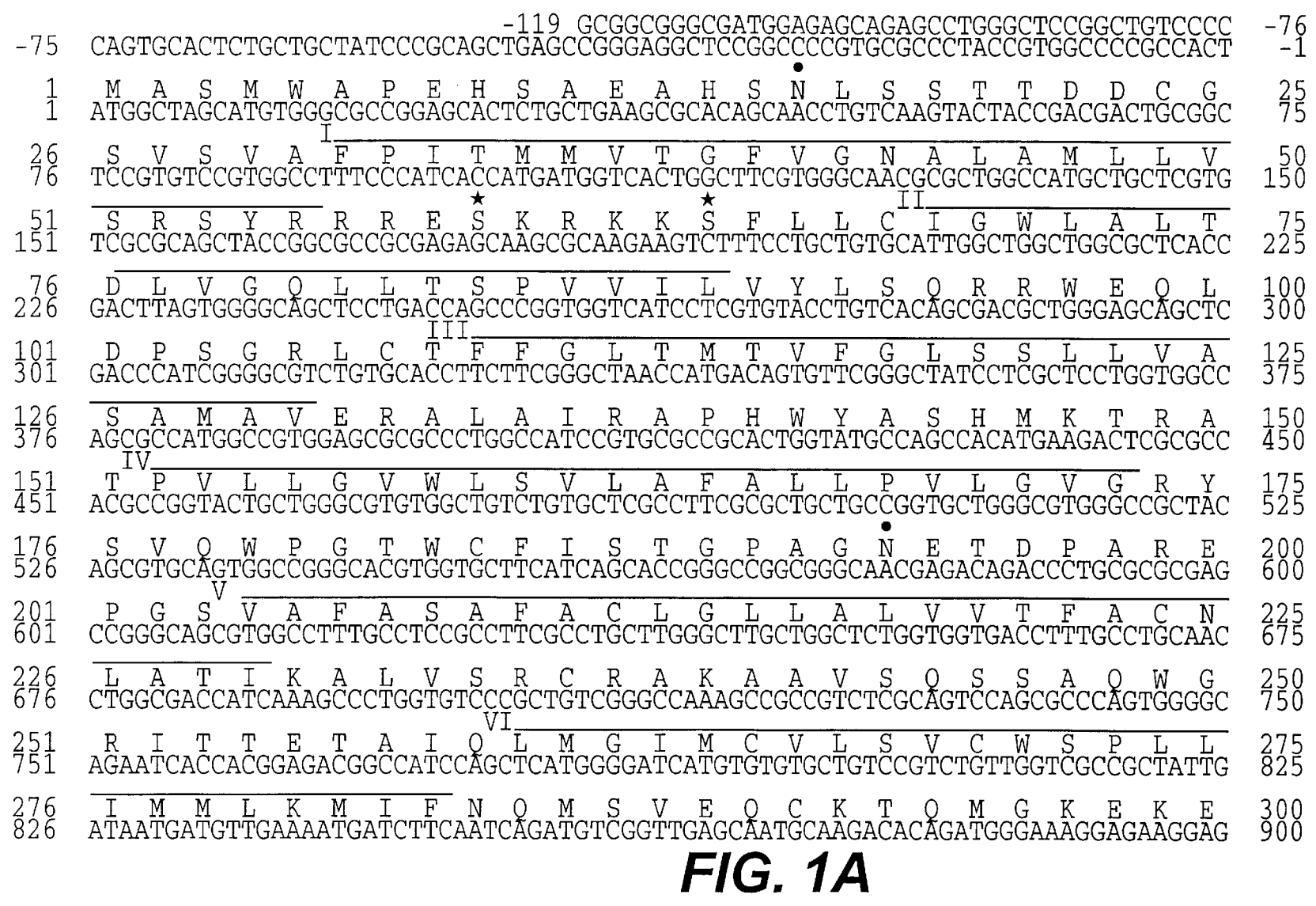
Figure 4A:
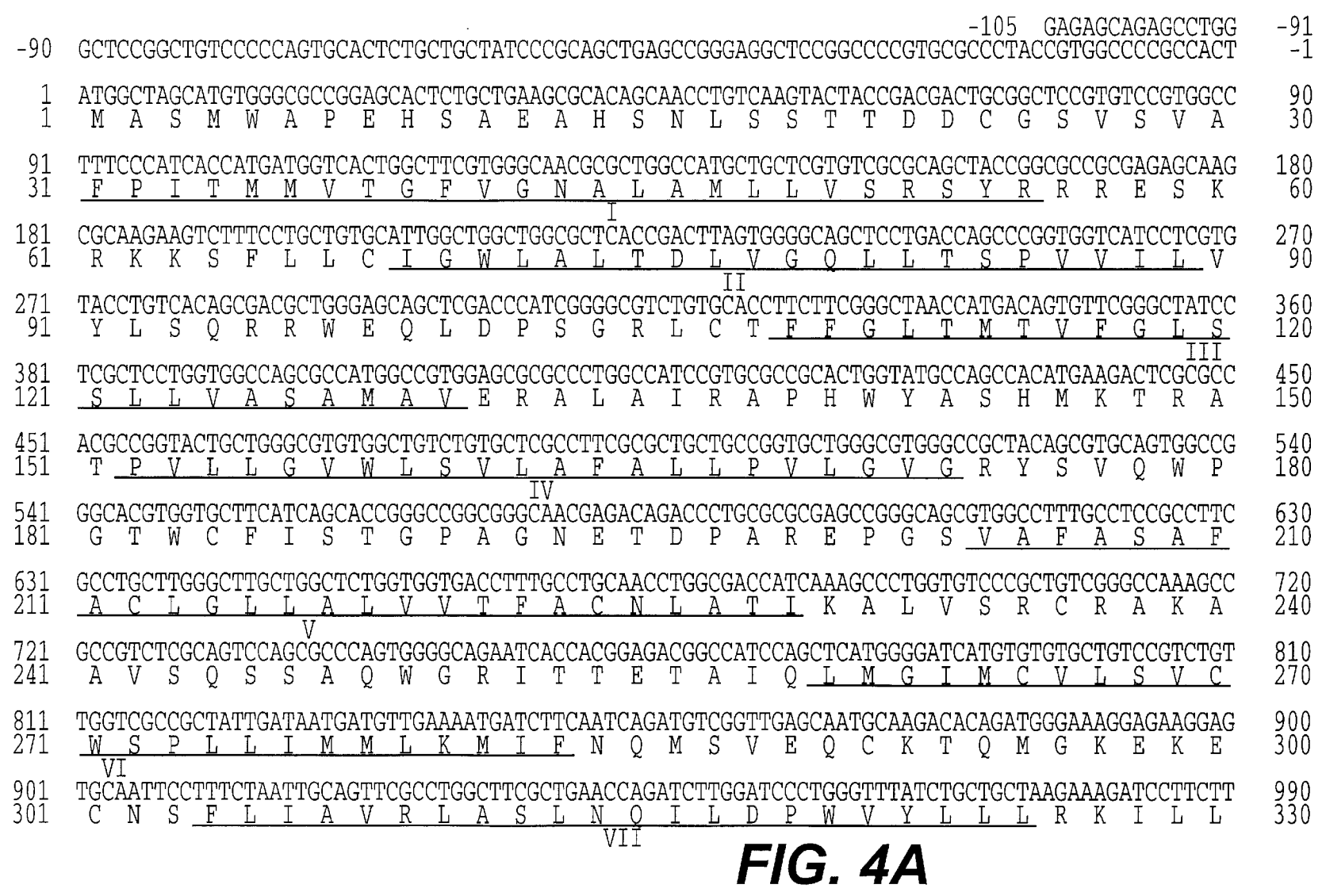
Figure 5:
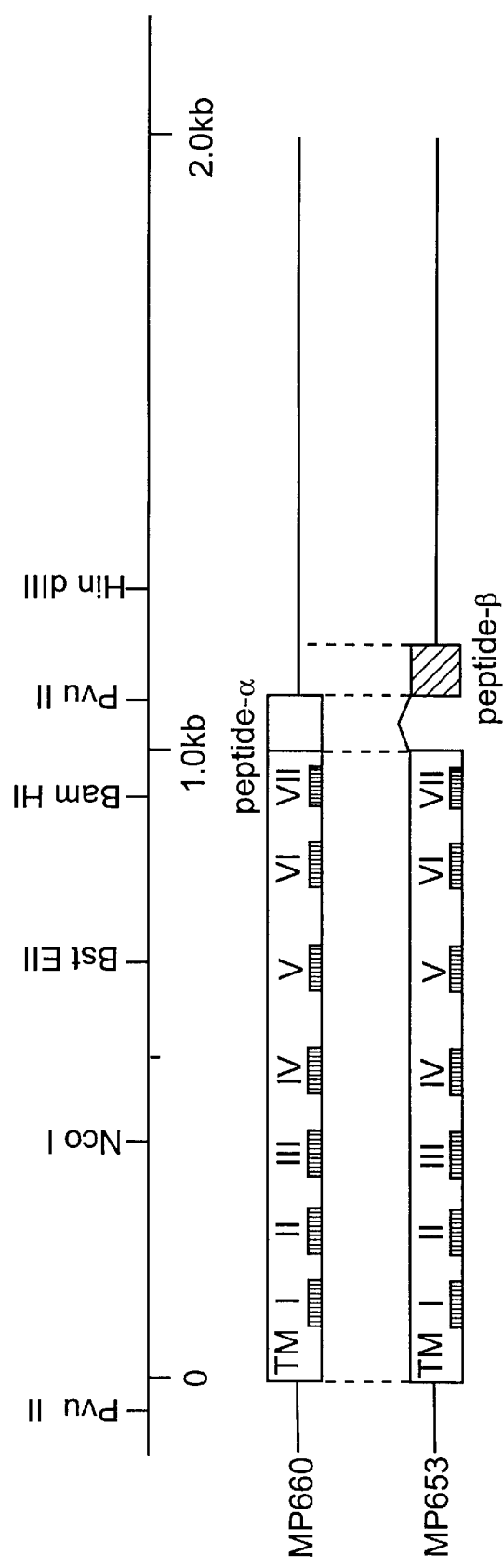
FIG. 5 shows comparison of cDNA structures of two $EP_3$ receptor isoforms. (Schematic representation of mouse $EP_3$ receptor cDNA clones, MP660 and MP653. Boxes represent coding sequences; open box is a corresponding coding sequence between the two cDNA, grey one is the sequence coding peptide-α, hatched one is the sequence coding peptide-β. The putative transmembrane domains are indicated by striped boxes.)

PGE$_2$ receptors of the mouse type include a polypeptide having the amino acid sequence comprising a series of the amino acid sequence of FIG. 1, (SEQ ID NO:2) a polypeptide having the amino acid sequence comprising a series of the amino acid sequence of FIG. 4 (SEQ ID NO:4) and a polypeptide having the amino acid sequence comprising a series of the amino acid sequence of FIG. 5. Any PGE$_2$ receptor is acceptable, as long as it is capable of receiving PGE$_2$ and activating GTP-binding protein. The receptor-G protein coupling may be examined in several ways. One example is to examine modulation of the finding affinity of the receptor by guanine nucleotides (Ann. Rev. Biochem. 56, 615–649 (1987)). Specifically, it may be a mutein resulting from deletion of at least one constituent amino acid from said amino acid sequence, replacement of at least one constituent amino acid by another amino acid, or addition of at least one amino acid, and may be a functional fragment.

The PGE receptor subtype may be of EP$_1$, EP$_2$ or EP$_3$ (α, β), with preference given to the EP$_2$ receptor and the EP$_3$ receptor.

The gene which codes for the PGE receptor may be any one, as long as it codes for the PGE receptor. For example, the gene which codes for the EP$_{3\alpha}$ receptor, a mouse PGE$_2$ receptor subtype, the gene which codes for the EP$_{3\beta}$ receptor, a mouse PGE$_2$ receptor subtype and the gene which codes for the EP$_2$ receptor, a mouse PGE$_2$ receptor subtype are exemplified by a gene having the base sequence comprising a series of the 1-1095 bases shown in FIG. 1, (SEQ ID NO:1) a gene having the base sequence comprising a series of the 1-1083 bases shown in FIG. 4 and a gene having the base sequence (SEQ ID NO:3) comprising a series of the 1-1539 bases shown in FIG. 5, respectively.

The vector according to the present invention, which harbors a recombinant DNA containing a gene which codes for PGE receptor, can, for example, be produced by:

(1) separating the RNA which codes for the PGE receptor,
(2) synthesizing a single-stranded complementary DNA (cDNA) and then a double-stranded DNA from said RNA,
(3) inserting said double-stranded DNA to a plasmid,
(4) transforming a host with the thus-obtained recombinant plasmid,
(5) cultivating the thus-obtained transformant and then isolating the plasmid containing the desired DNA therefrom by an appropriate method (e.g., colony hybridization using a DNA probe),
(6) cleaving out the desired cloned DNA from said plasmid, and
(7) ligating said cloned DNA to the downstream of the promoter in the vehicle.

Said cDNA can also be produced by chemical synthesis.

The RNA which codes for the PGE receptor can be obtained from various PGE-receptor-expressing cells known to those of ordinary skill in the art, such as mouse mastocytoma line P-815 cells and IL-3 dependent cell line BNu-cl3 cells.

Methods of preparing RNA from PGE-receptor-expressing cells include the guanidine thiocyanate method [J. M. Chirgwin et al., Biochemistry, 18, 5294 (1979)]. Other suitable methods known to those skilled within this art are also within this invention.

Using the thus-obtained RNA as a template in combination with reverse transcriptase, a cDNA is synthesized in accordance with, for example, the method of H. Okayama et al. [Molecular and Cellular Biology, 2, 161 (1982) and 3, 280 (1983)], and the resulting cDNA is inserted to a plasmid. Other methods for recombinantly synthesizing cDNA, known to those skilled in the art are also within the claimed invention.

Examples of the plasmid for cDNA insertion include plasmids derived from *Escherichia coli* such as pBR322 [Gene, 2, 95 (1977)], pBR325 [Gene, 4, 121 (1978)], pUC12 [Gene, 19, 259 (1982)], pUC13 [Gene, 19, 259 (1982)], pUC118 and pUC119 [Methods in Enzymology, 153, 3–11 (1987)] and those derived from *Bacillus subtilis* such as pUB110 [Biochemical and Biophysical Research Communications, 112, 678 (1983)], but any other can be used for this purpose, as long as it is replicable in the host.

Examples of the method of insertion to the plasmid include that described by T. Maniatis et al. in Molecular Cloning, Cold Spring Harbor Laboratory, page 239 (1982).

The plasmid incorporating said cDNA may be a plasmid obtained by using a cDNA library with *Escherichia coli* x1776 host prepared by inserting a cDNA synthesized from human normal diploid cell mRNA to the pCD vector [see Okayama et al., Molecular Cell Biology, 3, 280 (1983)], which cDNA library is available from Dr. Okayama at the Research Institute for Microbial Diseases, Osaka University.

The plasmid thus obtained is introduced to an appropriate host such as a bacterium of the genus Escherichia or Bacillus.

Example bacteria of the genus Escherichia include *Escherichia coli* K12DH1 [Proceedings of the National Academy of Science, USA, 60, 160 (1968)], M103 [Nucleic Acids Research, 9, 309 (1981)], JA221 [Journal of Molecular Biology, 120, 517 (1978)], HB101 [Journal of Molecular Biology, 41, 459 (1969)] and C600 [Genetics, 39,440 (1954)].

Example bacteria of the genus Bacillus include *Bacillus subtilis* MI114 [Gene, 24, 255 (1983)] and 207–21 [Journal of Biochemistry, 95, 87 (1984)].

Methods of transformation include the calcium chloride method and calcium chloride/rubidium chloride method described by T. Maniatis in Molecular Cloning, Cold Spring Harbor Laboratory, page 249 (1982).

From the transformants thus obtained, the desired clone is selected using a known method, such as colony hybridization [Gene, 10, 63 (1980)] or DNA base sequencing [Proceedings of the National Academy of Science, USA, 74, 560 (1977); Nucleic Acids Research, 9, 309 (1981)].

A microorganism carrying a vector having a cloned DNA containing a base sequence which codes for the PGE receptor is thus obtained.

Next, the plasmid is isolated from the microorganism.

Methods of such isolation include but are not limited to the alkali method [H. C. Birmboim et al., Nucleic Acids Research, 1, 1513 (1979)].

The above plasmid having a cloned recombinant DNA containing a gene which codes for the PGE receptor can be used as such or after being cleaved out with restriction enzyme as necessary.

The cloned gene is ligated downstream of a promoter, in a vehicle (vector) suitable for its expression, to yield an expression vector.

Example vectors include the above-mentioned plasmids derived from Escherichia coli (e.g., pBR322, pBR325, pUC12, pUC13, pUC118, pUC119), plasmids derived from *Bacillus subtilis* (e.g., pUB110, pTP5, pC194), yeast-derived plasmids (e.g., pSH19, pSH15), bacteriophages such as λ phage, animal viruses such as retrovirus and vaccinia virus and plasmids for animal expression (e.g., pcDNAI, pdKCR-dhfr).

The gene may have ATG (base sequence which codes for an appropriate signal peptide as desired) as a translational initiation codon at its 5'-terminal and TAA, TGA or TAG (preferably TGA) as a translational termination codon at its 3'-terminal. To express the gene, a promoter is ligated to the upstream thereof. Any promoter can be used for the present invention, as long as it is appropriate for the host used to express the gene.

Examples of preferred promoters include the T7 promoter, trp promoter, lac promoter, rec A promoter, λPL promoter or lpp promoter, when the transformation host is a bacterium of the genus Escherichia; the SPO1 promoter, SPO2 promoter or pen P promoter when the host is a bacterium of the genus Bacillus; and the PHO5 promoter, PGK promoter, GAP promoter or ADH promoter when the host is a yeast. Preference is given to the case in which a bacterium of the genus Escherichia is used as host in combination with the trp promoter or T7 promoter.

When the host is an animal cell, preferable promoters include the SV40-derived promoter and retrovirus promoter, with preference given to the SV40-derived promoter.

The thus-constructed vector, harboring a DNA, is used to produce a transformant.

Examples of the host include bacteria of the genus Escherichia, bacteria of the genus Bacillus, yeasts and animal cells. Examples of the bacteria of the genus Escherichia and of the genus Bacillus include the same as specified above.

Examples of the yeasts include *Saccharomyces cerevisiae* AH22R, NA87-11A and DKD-5D.

Example animal cells include simian cells COS-7, Vero, Chinese hamster ovarian cells CHO, mouse L cells and human FL cells.

The bacteria of the genus Escherichia can be transformed in accordance with the method described in the Proceedings of the National Academy of Science, USA, 69, 2110 (1972), Gene, 17, 107 (1982) and other publications known to those skilled in the art.

Bacteria of the genus Bacillus can be transformed in accordance with the method described in Molecular and General Genetics, 168, 111 (1979) and other publications, for instance.

Yeasts can be transformed in accordance with the method described in the Proceedings of the National Academy of Science, USA, 75, 1929 (1978), for instance.

Animal cells can be transformed in accordance with the method described in Virology, 52, 456 (1973), for instance.

A transformant resulting from transformation with a vector harboring the cDNA of PGE receptor is thus obtained.

For cultivating a transformant whose host is a bacterium of the genus Escherichia or Bacillus, it is appropriate to use a liquid medium supplemented with carbon sources, nitrogen sources, minerals and other substances necessary for the growth of the transformant. Example carbon sources include glucose, dextrin, soluble starch and sucrose. Example nitrogen sources include organic or inorganic substances such as ammonium salts, nitrates, corn steep liquor, peptone, casein, meat extract, soybean cake and potato extract. Example minerals include calcium chloride, sodium dihydrogen phosphate and magnesium chloride. Yeasts, vitamins, growth promoters and other additives may be added.

The pH of the medium is preferably about 6 to 8.

Examples of media preferably used to cultivate Escherichia bacteria include the M9 medium containing glucose and casamino acid [Miller, Journal of Experiments in Molecular Genetics, 431–433, Cold Spring Harbor Laboratory, New York (1972)]. To increase promoter efficiency as necessary, a chemical agent such as 3β-indolyl acrylic acid may be added.

When the host is a bacterium of the genus Escherichia, cultivation is normally carried out at about 15° to 43° C. for about 3 to 24 hours, with aeration and/or stirring as necessary.

When the host is a bacterium of the genus Bacillus, cultivation is normally carried out at about 30° to 40° C. for about 6 to 24 hours, with aeration and/or stirring as necessary.

Examples of media for cultivating a transformant whose host is a yeast include Burkholder's minimal medium [Bostian, K. L. et al., Proceedings of the National Academy of Science, USA, 77, 4505 (1980)]. It is preferable to adjust the medium to a pH of about 5 to 8. Cultivation is normally carried out at about 20° to 35° C. for 24 to 72 hours, with aeration and/or stirring as necessary.

Examples of media for cultivating a transformant whose host is an animal cell include MEM medium [Science, 122, 501 (1952)], DMEM medium [Virology, 8, 396 (1959)], RPMI1640 medium [Journal of the American Medical Association, 199, 519 (1967)] and 199 medium [Proceedings of the Society for the Biological Medicine, 73, 1 (1950)]. These media may be supplemented with about 5 to 20% fetal bovine serum. The pH is preferably about 6 to 8. Cultivation is normally carried out at about 30° to 40° C. for 15 to 60 hours, with aeration and/or stirring as necessary.

Separation and purification of PGE receptor of the present invention from the culture described above can, for example, be achieved as follows:

In extracting the PGE receptor of the present invention from cultured bacterial, yeast or animal cells, the cells are collected by a known method after cultivation and suspended in a buffer containing a protein denaturant, such as guanidine hydrochloride, to elute the desired PGE receptor extracellularly. In another method, the cells are disrupted by ultrasonication, lysozyme treatment and/or freeze-thawing, after which they are centrifuged to separate the PGE receptor of the invention. The method using a combination of lysozyme and ultrasonication is preferred.

For purifying the PGE receptor of the present invention from the supernatant, known methods of separation and purification can be used in combination as appropriate. Such known methods of separation and purification include those based on solubility differences such as salting-out and solvent precipitation, those based mainly on molecular weight differences such as dialysis, ultrafiltration, gel filtration and SDS-polyacrylamide gel electrophoresis, those based on charge differences such as ion exchange chromatography, those based on specific affinity such as affinity chromatography, those based on hydrophobicity differences such as reverse-phase high performance liquid chromatography, and those based on isoelectric point differences such as isoelectric focusing.

The thus-obtained PGE receptor of the present invention may be prepared as a dry powder by dialysis and lyophilization. It is appropriate to add serum albumin etc. as a carrier in storing the PGE receptor, since its adsorption to the container is prevented.

The PGE receptor of the present invention, substantially pure, is thus obtained. The substantially pure protein of the present invention has a protein content of not less than 95% (w/w), preferably not less than 98% (w/w).

The PGE receptor thus obtained itself, or a transformant expressing it or a moiety thereof can be used to screen substances exhibiting antagonistic or agonistic activity thereon by, for example, a ligand-binding test. The PGE receptor, as such, can also be used as a PGE-masking protein. The transformant obtained according to the present invention, which expressed the PGE receptor, and parts thereof can be efficiently used to obtain antibodies against said receptor.

Abbreviations for bases, amino acids, solvents and others used in the present specification and drawings attached thereto are based on abbreviations specified by the IUPAC-IUB Commission on Biochemical Nomenclature or abbreviations in common use in relevant fields. Some examples are given below. When an optical isomer may be present in amino acid, it is of the L-configuration, unless otherwise stated. These abbreviations may represent residues of corresponding compounds capable of forming a peptide bond.

DNA: Deoxyribonucleic acid
cDNA: Complementary deoxyribonucleic acid
A: Adenine
T: Thymine
G: Guanine
C: Cytosine
RNA: Ribonucleic acid
mRNA: Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediaminetetraacetic acid
SDS: Sodium dodecyl sulfate
Gly or G: Glycine
Ala or A: Alanine
Val or V: Valine
Leu or L: Leucine
Ile or I: Isoleucine
Ser or S: Serine
Thr or T: Threonine
Cys or C: Cysteine
Met or M: Methionine
Glu or E: Glutamic acid
Gln or Q: Glutamine
Asp or D: Aspartic acid
Lys or K: Lysine
Arg or R: Arginine
His or H: Histidine
Phe or F: Phenylalanine
Tyr or Y: Tyrosine
Trp or W: Tryptophan
Pro or P: Proline
Asn or N: Asparagine The present invention is hereinafter described in more detail by means of the following examples, which are not to be construed as limitative to the present invention.

The following clone cell lines which were obtained in the Examples mentioned below were deposited at the Institute for Fermentation, Osaka, Japan (IFO), and at the Fermentation Research Institute (National Institute of Bioscience and Human-Technology), Agency of Industrial Science and Technology, Ministry of International Trade and Industry, Japan (FRI) under the Budapest Treaty.

Their accession numbers on the deposit dates are shown in Table 1 below (The deposit dates are indicated in parenthesis)

TABLE 1

| Clone Cell line | IFO | FRI |
| --- | --- | --- |
| MP660/KCR (Example 1) | IFO 50366 (March 11, 1992) | FERM BP-3803 (March 18, 1992) |
| MP653/KCR (Example 2) | IFO 50397 (January 28, 1993) | FERM BP-4183 (February 10, 1993) |
| CHO/EP$_2$ (Example 4) | IFO 50396 (January 28, 1993) | FERM BP-4182 (February 10, 1993) |

EXAMPLE 1

(1) Amplification of Mouse cDNA Fragment Having Base Sequence Homology to human TXA$_2$ receptor cDNA by the PCR (polymerase chain reaction) method A single-stranded cDNA was synthesized from mouse lung total RNA by using random hexanucleotides as primers. PCR primers were designed based on the human TXA$_2$ receptor cDNA (HPL) sequences corresponding to the putative third and sixth transmenbrane domains of the receptor [M. Hirata et al., Nature 349, 617 (1991)]. Mouse lung cDNA served as template in 30 cycles of PCR with 1 min of denaturation at 95° C., 0.5 min of annealing at 60° C., and 1.5 min of extension at 72° C. on a Zymoreactor (Atto Corp., Tokyo, Japan). A single 418-base pair cDNA fragment was amplified and subcloned into pBluescript SK(+) (Stratagene). A clone isolated (LT3) showed a sequence 78% homologous to the corresponding region of the human cDNA (HPL).

(2) Cloning Mouse Prostaglandin E$_2$ Receptor (EP$_{3\alpha}$ cDNA

Mouse lung cDNA prepared by an oligo (dT) priming method was size-selected (>1.8 kilobases) and inserted into the EcoRI site of λ ZAPII DNA (Stratagene) with EcoRI adaptors (New England Biolabs, Inc.). The $1.9 \times 10^5$ clones derived from the cDNA library were screened by hybridization with LT3 obtained in (1) above. Hybridization was carried out at 58° C. in 6×SSC (900 mM NaCl and 90 mM sodium citrate) containing 5×Denhardt's solution (0.1% Ficoll, 0.1% polyvinylpyrrolidone, and 0.1% bovine serum albumin) and 0.5% sodium dodecyl sulfate, and filters were washed at 60° C. in 2×SSC containing 1% sodium dodecyl sulfate. Among several clones hybridizing positively to LT3, we picked up one (ML64) showing a signal apparently weaker than others. Using this clone as a hybridization probe, the cDNA library of mouse mastocytoma P-815 cells was screened for a full-length clone. From $7.2 \times 10^5$ clones of the P-815 λ ZAPII library, nine clones were isolated and subjected to sequence analysis. Nucleotide sequencing was carried out on double-stranded templates using the dideoxy chain termination method. A full-length DNA clone having a 1,095 bp open reading frame, MP660, was thus obtained. FIG. 1 shows the base sequence (SEQ ID NO:1) of the cDNA of MP660 and the amino acid sequence (SEQ ID NO:2) deduced therefrom. With respect to the amino acid sequence, the overlined portions, the sites marked with ★ and the sites marked with ● denote transmembrane domains I through VII, extracellular domain N-glycosylation sites and sites of phosphorylation by cAMP-dependent protein kinase, respectively.

(3) cDNA Expression in COS-1 Cells and Ligand-binding Test

Figure 2B:
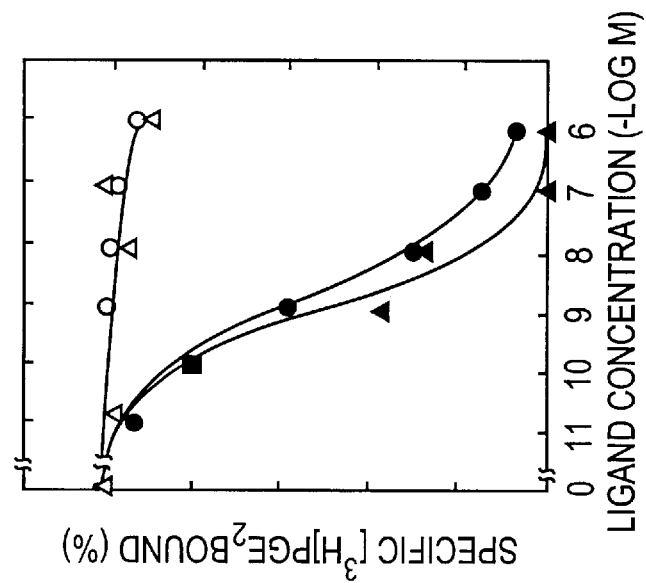
FIGS. 2(a) and (b) show the inhibitory activities of various ligands on the binding of [3H]-$PGE_2$ to the $PGE_2$ receptor ($EP_3$) expressed on MP660-transfected COS-1 cell membranes.
Figure 2A:
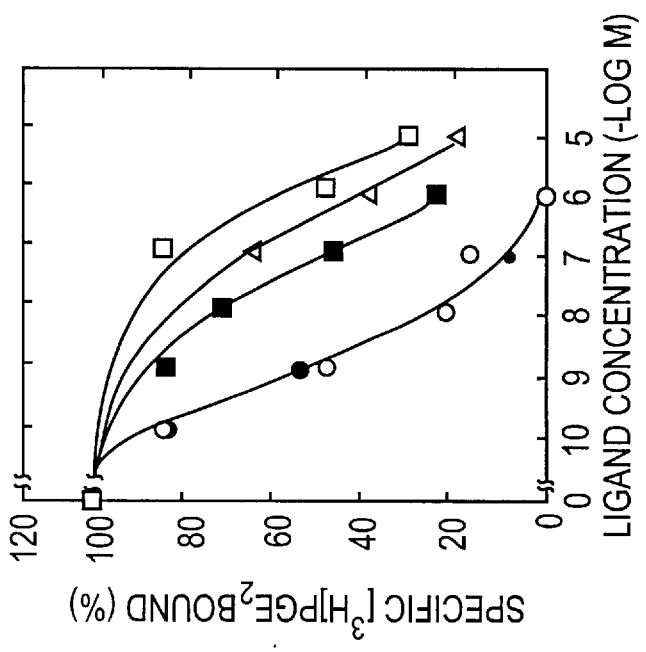

The cDNA of MP660 was cleaved out with EcoRI and inserted to pcDNAI (Invitrogen) and subcloned, followed by transfection of this plasmid DNA to COS-1 cells by the DEAE-dextran method [D. J. Sussmann and G. Milman, Mol. Cell. Biol., 4, 1641 (1984)]. After 72-hour cultivation, cells were harvested and cell membranes were separated [M. Hirata al., Nature, 349, 617 (1991)]. Using these cell membranes, various [3H]-labeled prosteglandins were assayed for binding activity; [3H]-$PGE_2$ was found to show specific binding. Also, the $PGE_2$ receptor obtained was identified as the subtype $EP_{3\alpha}$ receptor. FIG. 2 shows inhibitory activities of various ligands on the binding of [3H]-$PGE_2$ to the MP660-transfected cell membrane [Panel "a" is for inhibitory activities of various prostaglandins (○: $PGE_2$; ●: $PGE_1$; ■: iloprost; △: $PGF_{2\alpha}$; □: $PGD_2$); panel "b" is for inhibitory activities of prostaglandin-like substances (▲: M&B28,767; ●: GR63799X; △: butaprost; ○: SC-19220]. Specificity of this binding is shown in FIG. 2a. The binding of [$^3$H]$PGE_2$ was inhibited by unlabeled PGs in the order of $PGE_2=PGE_1>$iloprost, a $PGI_2$ analogue$>PGF_{2\alpha}>PGD_2$. Because PGE receptor is pharmacologically subdivided into three receptor subtypes, $EP_1$, $EP_2$, and $EP_3$, with different agonist and antagonist profiles, the specificity of this [$^3$H]$PGE_2$ binding using ligands specific for PGE receptor subtypes was further characterized. As shown in FIG. 2b, among various PGE analogues, only $EP_3$-specific agonists, GR 63799X and M&B 28,767, specifically competed for the[$^3$H]$PGE_2$ binding with equal potency, and they were more potent than $PGE_2$ itself. On the other hand, no competition was found at all with either an $EP_1$-specific antagonist, SC-19220, or an $EP_2$-specific agonist, butaprost. [$^3$H]$PGE_2$ did not bind to membranes of untransfected cells. These results established that MP660 encodes the $EP_3$ subtype of PGE receptor.

(4) Stable Expression and cAMP Assay of Receptor Gene

Figure 3:
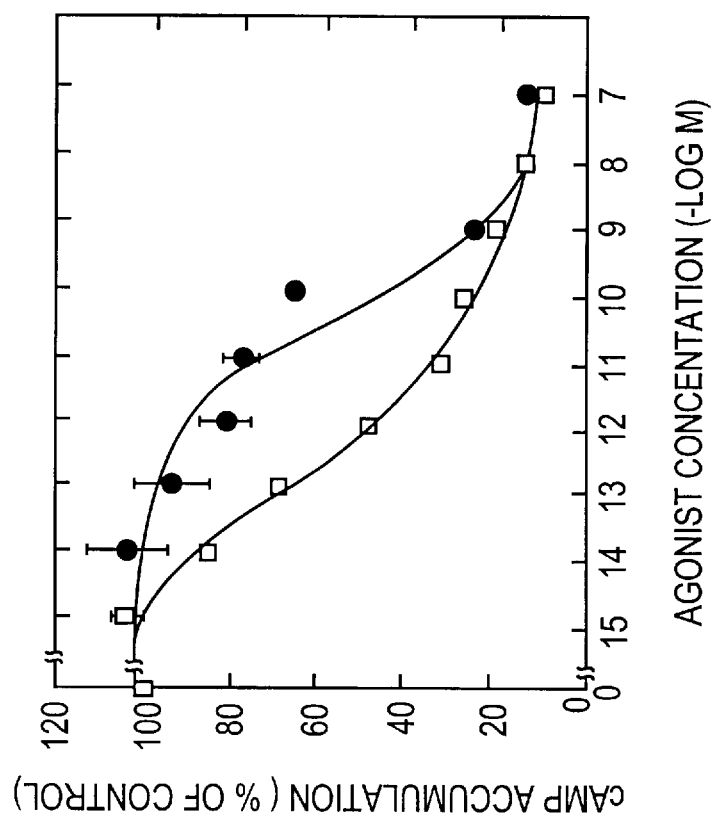
FIG. 3 shows the inhibitory activities of various ligands on the cAMP synthesis in CHO cells expressing the $PGE_2$ receptor.

To obtain cells that stably express the receptor gene, cDNA transfection was conducted by the method described by Nakajima et al. [J. Biol. Chem., 267, 2437 (1992)] to establish a cell line. Specifically, the EcoRI fragment of MP660 was inserted to pdKCR-dhfr [S. Oikawa et al., Biochem. Biophys. Res. Commun., 164, 39 (1989)], a eukaryotic cell expression vector having the mouse dhfr gene as a selection marker. This plasmid was transfected to CHO-dhfr (lacking dihydrofolate reductase activity) cells [G. Urlaub and L. A. Chasin, Proc. Natl. Acad. Sci. USA, 77, 4216 (1980)] by the calcium phosphate method [F. L. Graham and A. J. van der Eb, Virology, 52, 456 (1973)]. The cells were subjected to selection culture in α-modified Eagle's medium [S. Oikawa et al., Biochem. Biophys. Res. Commun., 164, 39 (1989)] which contained no ribonucleoside and deoxyribonucleoside and which contained 100 unit/ml penicillin, 100 μg/ml streptomycin and 10% dialyzed bovine fetal serum (Cell Culture Laboratories). The cells which proliferated were cloned and clone cells were obtained. $EP_{3\alpha}$ receptor cDNA transfection was confirmed by the RNA blotting method. Using thus-obtained CHO cells which constantly express the $EP_{3\alpha}$ receptor [MP660/KCR cells; IFO50366; FERM BP-3803], the effect of $PGE_2$ on forskolin-stimulated cAMP synthesis or M&B28,767, an $EP_3$-specific agonist was assessed. It was thus found that cAMP synthesis in MP660/KCR cells is inhibited by the co-presence of these substances (see FIG. 3; ●: $PGE_2$; □: M&B28,767). As shown in FIG. 3, the transfected CHO cells showed a dosedependent decrease to $PGE_2$ in forskolin-induced cellular cAMP accumulation. M&B 28,767, an $EP_3$-specific agonist, also inhibited forskolin-induced cAMP synthesis and was more potent than ($PGE_2$ ($IC_{50}$ of M&B 28,767=$1\times10^{-12}$M; $IC_{50}$ of $PGE_2$=$1\times10^{-10}$M).

(5) mRNA Expression in Various Tissues

Total RNAs from various mouse tissues were isolated by the acid guanidinium thiocyanate-phenol-chloroform method [P. Chomczynski and N. Sacchi, Anal. Biochem., 162, 156 (1987)]. Next, from this total RNAs, poly(A)+ RNAs were purified using Oligotex $dT_{30}$ (Takara Shuzo, Kyoto, Japan). Poly (A)$^+$ RNAs (10 μg) from each tissue were separated by electrophoresis on a 1.2% agarose gel, transferred onto nylon membranes (Hybond-N, Amersham Corp.), and hybridized with a $^{32}$P-labeled EcoRI/Bam HI fragment of MP660 clone. Hybridization was carried out at 68° C. in 6×SSC, and filters were washed at 68° C. in 1×SSC. Eventually, a 2.3 kb strong band appeared from tissues on which $PGE_2$ is pharmacologically active, such as the kidney, stomach and uterus, and from P-815 cells. Another band appeared near 7.0 kb from these tissues and cells.

EXAMPLE 2

(1) Cloning Mouse Prostaglandin $E_2$ Receptor ($EP_{3\beta}$) cDNA

In substantially the same screening method as in Example 1, using ML64 as a hybridization probe, several clones were isolated from mouse mastocytoma P-815 cDNA library. Restriction analysis of the isolated clones displayed at least two types of cDNAs, one type represented by MP660 obtained in Example 1 and another type represented by MP653. Sequencing analyses revealed that MP653 had a 1,083 base pair (bp) open reading frame. FIG. 4 shows the base sequence (SEQ ID NO:3) of the cDNA of MP653 and the amino acid sequence (SEQ ID NO:4) deduced therefrom as compared with those of MP660. MP653 is identical to MP660 in the nucleotide sequence except deletion of an 89-bp sequence in the coding region of the putative C-terminal tail of the receptor in MP660-encoded receptor (FIG. 5). Deletion of this 89-bp sequence creates another reading frame downstream from this junction, which extends coding region until a new stop codon placed on 77-bp downstream from the stop codon of MP660. As a consequence, a 30-amino-acid (aa) C-terminal fragment of the MP660-encoded receptor (peptide-α) was replaced with a new 26-aa fragment (peptide-β) in the C-terminal end of MP653-encoded receptor.

(2) Expression of the MP653 cDNA in COS-1 Cells and Ligand-binding Assay

The cDNA of MP653 was cleaved out with EcoRI and inserted to pcDNAI (Invitrogen) and subcloned, followed by transfection of this plasmid DNA to COS-1 cells by the DEAE-dextran method [D. J. Sussmann and G. Milman, Mol. Cell. Biol., 4, 1641 (1984)]. After 72-hour cultivation, cells were harvested and cell membranes were separated [M. Hirata et al., Nature, 349, 617 (1991)]. Using these cell membranes, various [$^3$H]-labeled prostaglandins were assayed for binding activity; [$^3$H]-PGE$_2$ was found to show specific binding. Also, the PGE$_2$ receptor obtained was identified as the subtype EP$_{3\beta}$ receptor. The result of inhibitory activities of various ligands on the binding of [$^3$H]-PGE$_2$ to the MP653-transfected cell membrane was substantially the same as on the binding of [$^3$H]-PGE$_2$ to the MP660—transfected cell membrane obtained in Example 1.

MP660—encoding receptor is designated as EP$_{3\alpha}$ (containing the peptide-α) and MP653-encoding one as EP$_{3\beta}$ (containing the peptide-β).

(3) Stable Expression and cAMP Assay of Receptor Gene

To obtain cells that stably express the receptor gene, cDNA transfection was conducted by the method described by Nakajima et al. [J. Biol. Chem., 267, 2437 (1992)] to establish a cell line. Specifically, the EcoRI fragment of MP653 was inserted to pdKCR-dhfr [S. Oikawa et al., Biochem. Biophys. Res. Commun., 164, 39 (1989)], a eukaryotic cell expression vector having the mouse dhfr gene as a selection marker. This plasmid was transfected to CHO-dhfr(lacking dihydrofolate reductase activity) cells [G. Urlaub and L. A. Chasin, Proc. Natl. Acad. Sci. USA, 77, 4216 (1980)] by the calcium phosphate method [(F. L. Graham and A. J. van der Eb, Virology, 52, 456 (1973)]. The cells were subjected to selection culture in α-modified Eagle's medium [S. Oikawa et al., Biochem. Biophys. Res. Commun., 164, 39 (1989)] which contained no ribonucleoside and deoxyribonucleoside and which contained 100 unit/ml penicillin, 100 μg/ml streptomycin and 10% dialyzed bovine fetal serum (Cell Culture Laboratories). The cells which proliferated were cloned to have clone cells. EP$_{3\beta}$ receptor cDNA transfection was confirmed by the RNA blotting method. Using thus-obtained CHO cells which constantly express the EP$_{3\beta}$ receptor [MP653/KCR cells; IFO 50397, FERM BP-4183], the effect of PGE$_2$ on forskolin-stimulated cAMP synthesis or M&B28, 767, an EP$_3$-specific agonist was assessed. It was thus found that cAMP synthesis in MP653/KCR cells is inhibited by the co-presence of these substances.

EXAMPLE 3
Expression of EP$_{3\alpha}$ and EP$_{3\beta}$ in Various Tissues

Measurement of the relative abundance of the two isoforms, EP$_{3\alpha}$ and EP$_{3\beta}$, expressed in each tissue was performed according to the method of Wang et al. (Proc. Natl. Acad. Sci. 86, 9717 (1989)). Total RNA was isolated according to Example 1 (5) and the RNAs were transcribed into cDNA by random hexanucleotide priming method using Moloney murine leukemia virus reverse transcriptase (Bethesda Research Laboratories). Each cDNA derived from 2.5 μg RNA was used as template in a PCR with primers corresponding to nucleotide positions 651–680 (PCR I) and 1264–1293 (PCR II). The 5'-end $^{32}$P-labeled PCR II (0.3 pmol; 1.0×10$^6$ c.p.m./pmol) was incubated in each PCR reaction (final 25 μl). Twenty-three cycles of PCR were performed using the following temperature profile: 94° C., 40 s; 60° C., 40 s; 72° C., 1.5 min. DNA-resolved gel was dried and subject to autoradiography, and the radioactivity of the gel corresponding to the bands was counted. Consequently, it was found that in any tissue expressing EP$_3$, EP$_{3\alpha}$ was dominantly expressed over EP$_{3\beta}$.

EXAMPLE 4
(1) Cloning Mouse Prostaglandin E$_2$ Receptor (EP$_2$) cDNA

Figure 6A:
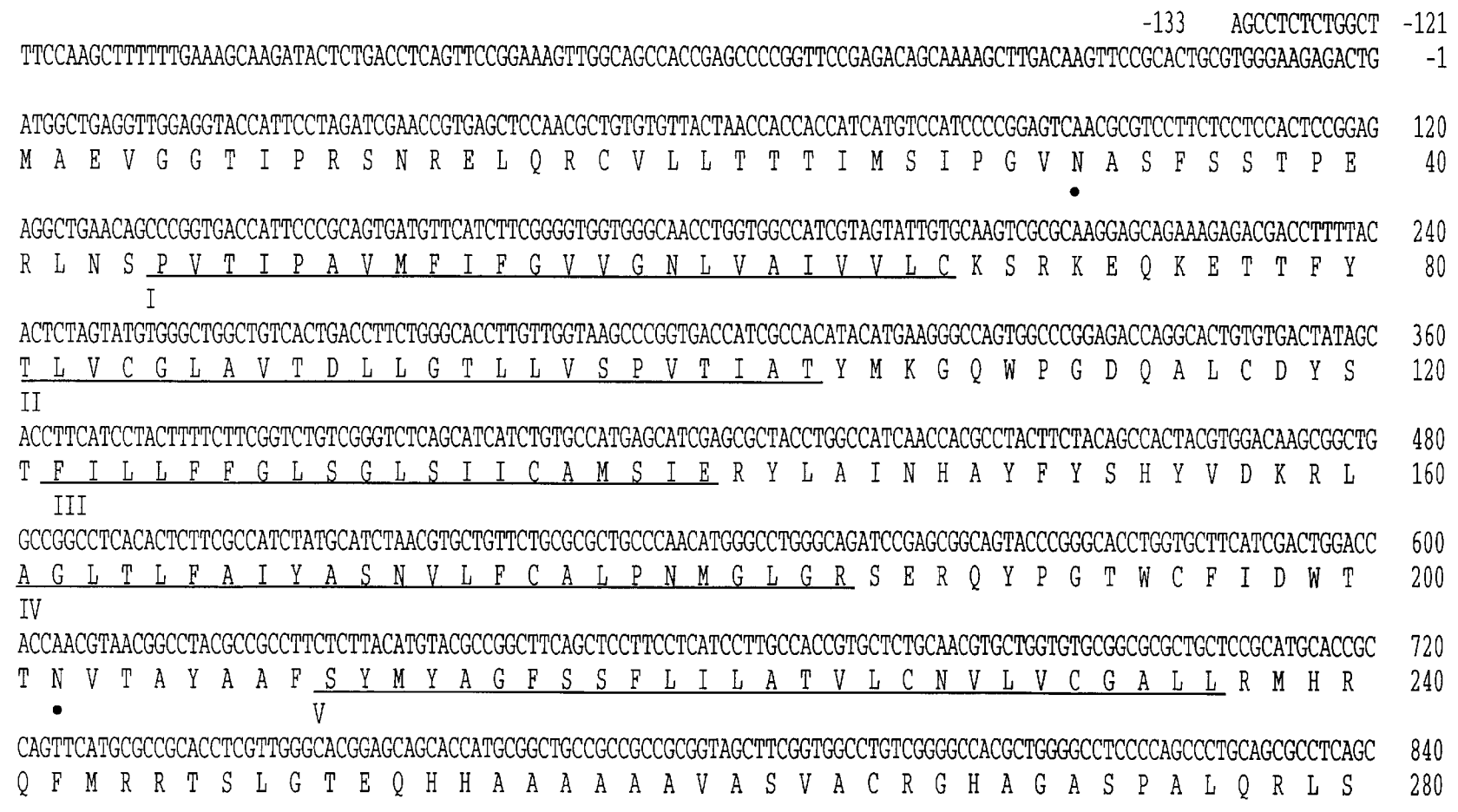

Mouse mastocytoma P-815 cell cDNA library carring cDNAs larger than 2.0 kb was prepared according to Example 1 (2). The probe DNA was prepared by PCR using mouse EP$_3$ cDNA as a template; this 482 bp fragment covers the transmembrane segments I–IV region of the EP$_3$ receptor. The 2.0×10$^5$ clones derived from the cDNA library were screened under either high (Sambrook) or low stringency condition. The resultant positive clones were subjected to PCR, restriction and sequence analyses and classified into two major groups; one group (six clones) belonged to EP$_3$ receptor cDNA, and the other (five clones) showed a sequence homologous but not identical to EP$_3$ cDNA. One representative clone (MP412) of the latter group, which contains a 1539-base pair open reading frame. FIG. 6 shows the base sequence (SEQ ID NO:5) of the cDNA of MP412 and the amino acid sequence (SEQ ID NO:6) deduced therefrom. This cDNA was transfected into COS-1 cells according to the same manner as in Example 1 (3).

(2) PGE$_2$ Binding and cAMP Assays in COS-1 Cells Expressing MP412 cDNA

Figure 8:
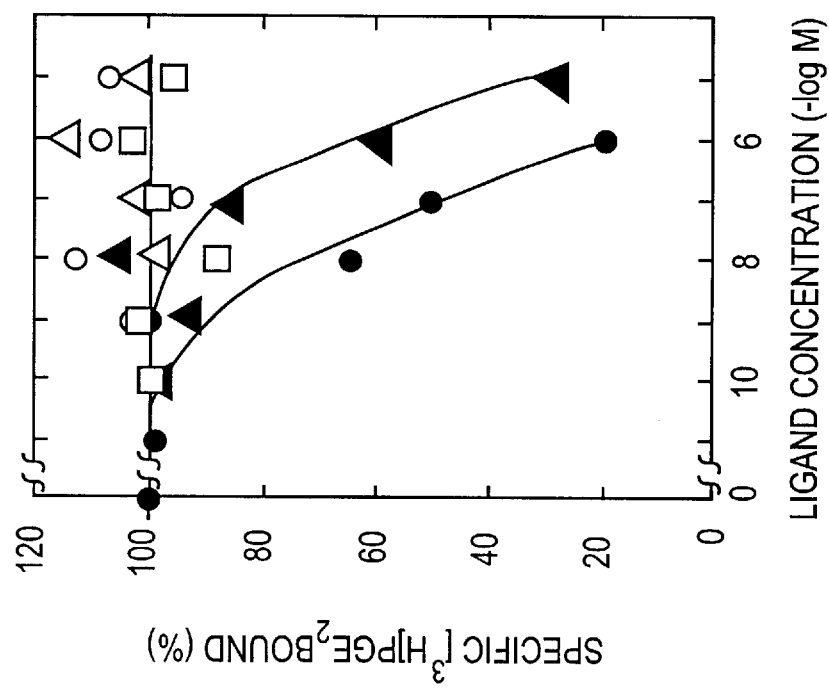
FIGS. 7 and 8 show the inhibitory activities of various ligands on the binding of [$^3$H]-PGE$_2$ to the PGE$_2$ receptor (EP$_2$) expressed on MP412-transfected COS-1 cell membrances.
Figure 7:
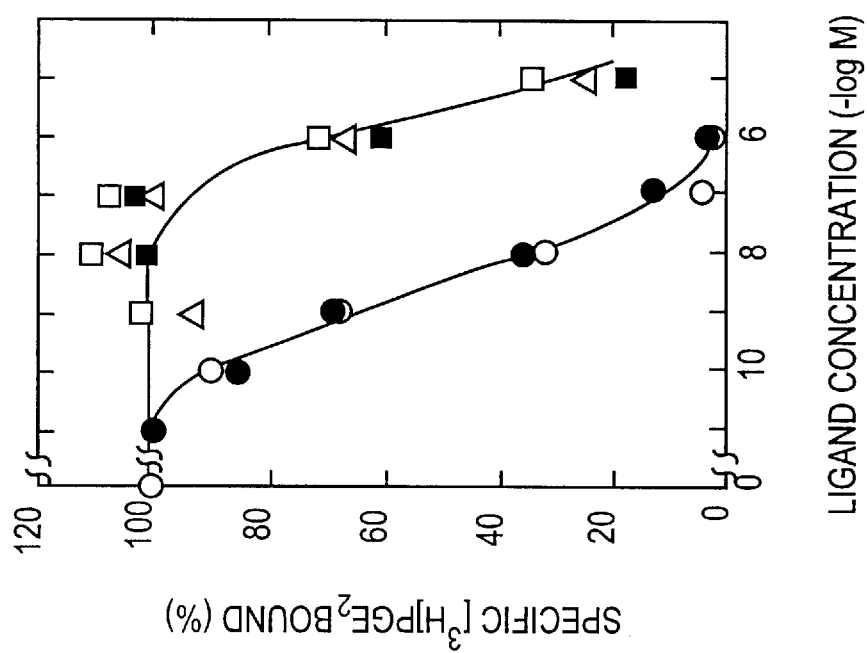

After the COS-1 cells carring the plasmid DNA obtained in above (1) were cultured for 72 h, cells were harvested and cell membranes were prepared. Using these cell membranes, various [$^3$H]-labeled prostaglandins were assayed for binding activity; [$^3$H]-PGE$_2$ was found to show specific binding. Specific [$^3$H]-PGE$_2$ binding to the membrane of untransfected cells was almost negligible. FIG. 7 shows the specificity of this binding. Specific [$^3$H]-PGE$_2$ binding was inhibited by unlabeled PG in the order of PGE$_2$(○)=PGE$_1$ (●)>>iloprost(■), a stable PGI$_2$ analogue ≧PGF$_{2\alpha}$(△)PGD$_2$ (□). FIG. 8 shows ligand binding specificity using several ligands which show characteristic agonist or antagonist activity for PGE receptor subtypes. As shown in FIG. 8, the PGE$_2$ binding was inhibited by misoprostol(●), an EP$_2$ and EP$_3$ agonist, and more weakly by M&B 28,767(▲), an EP$_3$ agonist. On the other hand, sulprostone (□), an EP$_1$ and EP$_3$ agonist, SC-19220(○), an EP$_1$ antagonist, and butaprost (△), an EP$_2$ agonist, did not inhibit it. The ability of misoprostol to inhibit PGE$_2$ binding and no ability of sulprostone suggest that MP412 encodes the EP$_2$ subtype of PGE receptor, and this was also supported by weak cross-reaction of M&B 28,767 to EP$_2$ (Lawrence, R. A. et al, Br. J. Pharmacol. 105, 271–278 (1992)). The lack of binding activity of butaprost in mouse EP$_2$ might indicate that the action of butaprost is species specific or there may be other forms of EP$_2$ receptor subtype.

Figure 9:
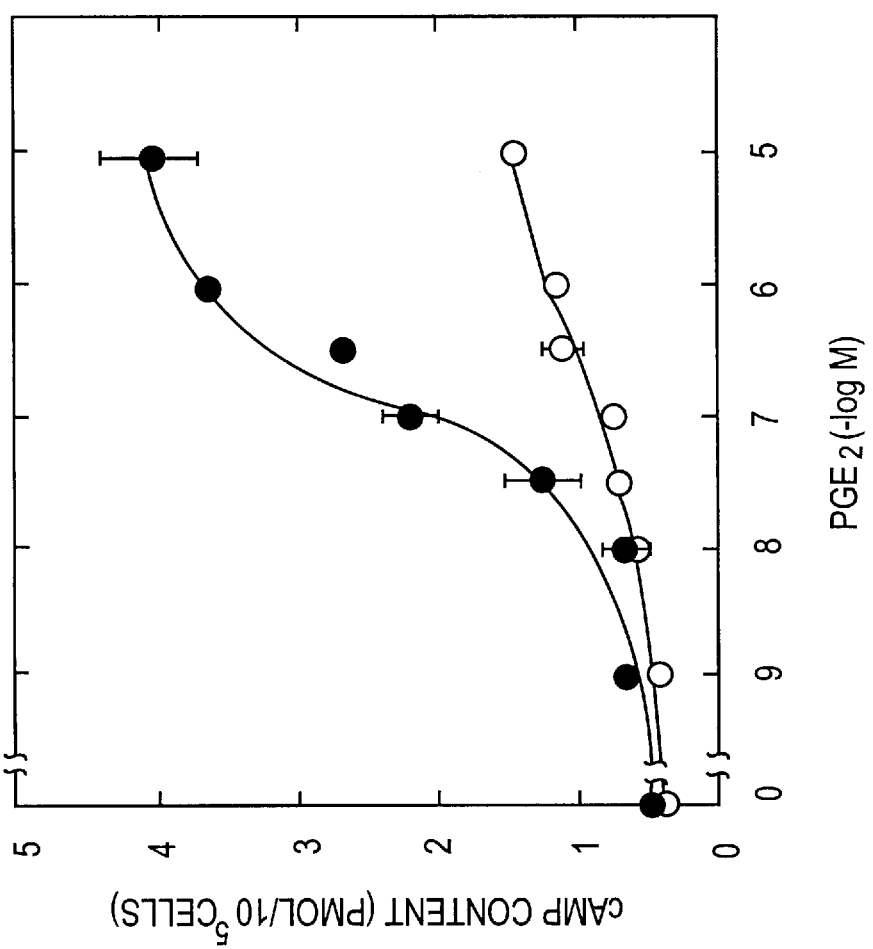
FIG. 9 shows the effect of PGE$_2$ on cAMP level in MP412-transfected or untransfected COS-1 cells.

EP$_2$ receptor is coupled to stimulation of adenylate cyclase. For cAMP assay, the plasmid DNA was transfected into COS-1 cells by the lipofection method (P. L. Felgner et al., Proc. Natl. Acad. Sci., 84, 7413 (1987)) and cultured for 72 h in a 24-well plate. Cyclic AMP levels in the cells were determined according to the method of Nakajima et al. (J. Biol. Chem. 267, 2437 (1992)). As shown in FIG. 9, PGE$_2$ dose-dependently increased cAMP level in these cells (●:MP412-transfected COS-1 cells; ○:untransfected COS-1 cells). On the other hand, PGE$_2$ neither inhibited forskolin-induced cAMP formation and nor accumulated inositol phosphates. These results demonstrate that this receptor is an EP$_2$ subtype coupled exclusively to stimulation of adenylate cyclase.

To obtain cells that stably express the receptor gene, cDNA transfection was conducted by the method according to Example 1 (4) to establish a cell line. Specifically, the EcoRI fragment of MP412 was inserted to pdKCR-dhfr, a eukaryotic cell expression vector having the mouse dhfr gene as a selection marker. This plasmid was transfected to CHO-dhfr. (lacking dihydrofolate reductase activity) cells. The cells were subjected to selection culture, the cells which proliferated were cloned to have clone cells, and thus the CHO cells which constantly express the EP$_2$ receptor [CHO/EP$_2$ cells; IFO 50396, FERM BP-4182] were obtained.

(3) mRNA Expression in Various Tissues

Poly (A)+ RNAs (10 μg) from each tissue, which were prepared by the same method as in Example 1 (5), were separated by electrophoresis on a 1.2% agarose gel, transferred onto nylon membranes (Hybond-N, Amersham Corp.), and hybridized with a $^{32}$P-labeled EcoRI/BamHI fragment of MP412 clone. Hybridization was carried out at 68° C. in 6×SSC, and filters were washed at 68° C. in 2×SSC. A positive band is observed at 3.9 kilobase in most of tissues, suggesting widespread distribution of the $EP_2$ receptor. The tissues highly expressing $EP_2$ mRNA were ileum and thymus in which $PGE_2$ induces relaxation of ileum circular muscle and inhibits proliferation of T cells by increasing intracellular cAMP levels. A significant band was also observed in lung, spleen, heart or uterus. On the other hand, $EP_2$ mRNA was not detectable in testis and liver.

Other embodiments of the invention will be apparent in the art from consideration of the specification and practice of the invention disclosed herein. It is intended that the specification and examples be considered as exemplary only, with a true scope and spirit of the invention being indicated by the following claims.

What is claimed is:

1. An isolated DNA encoding a prostaglandin E receptor comprising amino acids 1 to 361 of SEQ ID NO:4.

2. The DNA according to claim 1, which comprises nucleotides 106 to 1188 of SEQ ID NO:3.

3. An isolated DNA encoding a prostaglandin E receptor having the amino acid sequence set forth in SEQ ID No:4.

4. A vector comprising an isolated DNA encoding prostaglandin receptor comprising the amino acid sequence as set forth in SEQ ID NO:4.

5. A host cell transformed with the vector of claim 4.

6. A method for producing a prostaglandin E receptor which comprises cultivating the transformed host cell of claim 5 in a culture medium under conditions that would allow expression of the receptor, and recovering the receptor.

* * * * *

UNITED STATES PATENT AND TRADEMARK OFFICE
CERTIFICATE OF CORRECTION

PATENT NO.: 5,804,415

DATED: September 8, 1998

INVENTOR(S): Atsushi Ichikawa, Shuh Narumiya

It is certified that an error appears in the above-identified patent and that said Letters Patent is hereby corrected as shown below:

In claim 4, column 25, line 57, before "receptor", insert --E--.

Signed and Sealed this

Ninth Day of March, 1999

Attest:

Attesting Officer

Q. TODD DICKINSON

Acting Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 2107 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| GCGGCGGGCG | ATGGAGAGCA | GAGCCTGGGC | TCCGGCTGTC | CCCCAGTGCA | CTCTGCTGCT | 60 |
| ATCCCGCAGC | TGAGCCGGGA | GGCTCCGGCC | CCGTGCGCCC | TACCGTGGCC | CCGCCACTAT | 120 |
| GGCTAGCATG | TGGGCGCCGG | AGCACTCTGC | TGAAGCGCAC | AGCAACCTGT | CAAGTACTAC | 180 |
| CGACGACTGC | GGCTCCGTGT | CCGTGGCCTT | TCCCATCACC | ATGATGGTCA | CTGGCTTCGT | 240 |
| GGGCAACGCG | CTGGCCATGC | TGCTCGTGTC | GCGCAGCTAC | CGGCGCCGCG | AGAGCAAGCG | 300 |
| CAAGAAGTCT | TTCCTGCTGT | GCATTGGCTG | GCTGGCGCTC | ACCGACTTAG | TGGGCAGCT | 360 |
| CCTGACCAGC | CCGGTGGTCA | TCCTCGTGTA | CCTGTCACAG | CGACGCTGGG | AGCAGCTCGA | 420 |
| CCCATCGGGG | CGTCTGTGCA | CCTTCTTCGG | GCTAACCATG | ACAGTGTTCG | GGCTATCCTC | 480 |
| GCTCCTGGTG | GCCAGCGCCA | TGGCCGTGGA | GCGCGCCCTG | GCCATCCGTG | CGCCGCACTG | 540 |
| GTATGCCAGC | CACATGAAGA | CTCGCGCCAC | GCCGGTACTG | CTGGGCGTGT | GGCTGTCTGT | 600 |
| GCTCGCCTTC | GCGCTGCTGC | CGGTGCTGGG | CGTGGGCCGC | TACAGCGTGC | AGTGGCCGGG | 660 |
| CACGTGGTGC | TTCATCAGCA | CCGGGCCGGC | GGGCAACGAG | ACAGACCCTG | CGCGCGAGCC | 720 |
| GGGCAGCGTG | GCCTTTGCCT | CCGCCTTCGC | CTGCTTGGGC | TTGCTGGCTC | TGGTGGTGAC | 780 |
| CTTTGCCTGC | AACCTGGCGA | CCATCAAAGC | CCTGGTGTCC | CGCTGTCGGG | CCAAAGCCGC | 840 |
| CGTCTCGCAG | TCCAGCGCCC | AGTGGGGCAG | AATCACCACG | GAGACGGCCA | TCCAGCTCAT | 900 |
| GGGGATCATG | TGTGTGCTGT | CCGTCTGTTG | GTCGCCGCTA | TTGATAATGA | TGTTGAAAAT | 960 |
| GATCTTCAAT | CAGATGTCGG | TTGAGCAATG | CAAGACACAG | ATGGGAAAGG | AGAAGGAGTG | 1020 |
| CAATTCCTTT | CTAATTGCAG | TTCGCCTGGC | TTCGCTGAAC | CAGATCTTGG | ATCCCTGGGT | 1080 |
| TTATCTGCTG | CTAAGAAAGA | TCCTTCTTCG | GAAGTTCTGC | CAGATCAGAG | ACCACACCAA | 1140 |
| CTATGCTTCC | AGCTCCACCT | CCTTGCCCTG | CCCAGGCTCC | TCAGCCCTGA | TGTGGAGTGA | 1200 |
| CCAGCTGGAA | AGATGATGAA | CAACCTGAAG | TGGACTTTCA | TTGCAGTACC | TGTTTCCCTG | 1260 |
| GGTCTGAGAA | TTTCTTCTCC | CAGGGAAGGA | TGACTGAGTA | TTTTGGATTG | TATCTTCTTT | 1320 |
| TGGCCTCAAT | TTTAAGTTTT | CCTTGCCATT | AAACACACCG | AGACAAGCTT | TCTTAGGATA | 1380 |

-continued

```
ATCTGAGAGT CTGGTTGTTA GCTGGTTCCT GTGAAGACTG AAGACTCTGC ACTTGAGACG    1440

GGGGCAAGAC GACACAGAGC AGCATGGAGA GACTCAGTGC AGAAATATCT CCAGCCTCAG    1500

AACCTTTGTG GACATGGACA CCTTCATGTA TTGATAGTCT GACTCTTCTA AATAGGTCTG    1560

AAAAAGCAGC ATAAGTTTTT AAACAGTGAA GCATCAATGT GTTGAGAGCA ATGTTCATC     1620

TAATAAGCCA TGAGCCAAAC AAGACAAAAA GTCTACATGA GAGGCAAGAG AGATTCTGCA    1680

AAGGGTATTT GTGCCAAGAA GGTATACAGT ACCACAGAGT TGTGTCCTCA GTGAGAGTGG    1740

GAAATAAGTT TCTAATTTAA TTCTAATTAC TGGCTCCTCA GTAATTCAGG AATCGTGCCA    1800

TCATTTCCCT GCTTTTAAAG GGAGAAGTTT AGCTAAAGAC ACATTCCAGG TGTCACTAAC    1860

AGTTCCAAAG CTAGGTGACT AAATGTTCAG CTAGAGCTGT TAAAAGGAAA ACCAGCTAAT    1920

TATCATTCCA GTCCAATGCT ATTTTTGAAT TACTATCTAC TTAAGATTTC TCATAATTTG    1980

TGCTCAGGCA GCACAATAAA AAGGGGGGGG CAAAATTACT AAGTGACAGT TATTCTGCAT    2040

CTAAGTCTGT GACTTTTTTA TGAAATAAAA TGATTTTGTC TGTGTTGAAA TAAAAAAAAA    2100

AAAAAAA                                                               2107
```

( 2 ) INFORMATION FOR SEQ ID NO:2:

( i ) SEQUENCE CHARACTERISTICS:
    ( A ) LENGTH: 365 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:2:

```
Met Ala Ser Met Trp Ala Pro Glu His Ser Ala Glu Ala His Ser Asn
 1               5                  10                  15

Leu Ser Ser Thr Thr Asp Asp Cys Gly Ser Val Ser Val Ala Phe Pro
             20                  25                  30

Ile Thr Met Met Val Thr Gly Phe Val Gly Asn Ala Leu Ala Met Leu
                 35                  40                  45

Leu Val Ser Arg Ser Tyr Arg Arg Arg Glu Ser Lys Arg Lys Lys Ser
     50                  55                  60

Phe Leu Leu Cys Ile Gly Trp Leu Ala Leu Thr Asp Leu Val Gly Gln
 65                  70                  75                  80

Leu Leu Thr Ser Pro Val Val Ile Leu Val Tyr Leu Ser Gln Arg Arg
                 85                  90                  95

Trp Glu Gln Leu Asp Pro Ser Gly Arg Leu Cys Thr Phe Phe Gly Leu
             100                 105                 110

Thr Met Thr Val Phe Gly Leu Ser Ser Leu Leu Val Ala Ser Ala Met
         115                 120                 125

Ala Val Glu Arg Ala Leu Ala Ile Arg Ala Pro His Trp Tyr Ala Ser
     130                 135                 140

His Met Lys Thr Arg Ala Thr Pro Val Leu Leu Gly Val Trp Leu Ser
145                 150                 155                 160

Val Leu Ala Phe Ala Leu Leu Pro Val Leu Gly Val Gly Arg Tyr Ser
                 165                 170                 175

Val Gln Trp Pro Gly Thr Trp Cys Phe Ile Ser Thr Gly Pro Ala Gly
             180                 185                 190

Asn Glu Thr Asp Pro Ala Arg Glu Pro Gly Ser Val Ala Phe Ala Ser
         195                 200                 205

Ala Phe Ala Cys Leu Gly Leu Leu Ala Leu Val Val Thr Phe Ala Cys
     210                 215                 220
```

| | | | | | | | | | | | | | | |
|---|---|---|---|---|---|---|---|---|---|---|---|---|---|---|
| Asn | Leu | Ala | Thr | Ile | Lys | Ala | Leu | Val | Ser | Arg | Cys | Arg | Ala | Lys | Ala |
| 225 | | | | 230 | | | | | 235 | | | | | 240 |
| Ala | Val | Ser | Gln | Ser | Ser | Ala | Gln | Trp | Gly | Arg | Ile | Thr | Thr | Glu | Thr |
| | | | | 245 | | | | | 250 | | | | | 255 | |
| Ala | Ile | Gln | Leu | Met | Gly | Ile | Met | Cys | Val | Leu | Ser | Val | Cys | Trp | Ser |
| | | | 260 | | | | | 265 | | | | | 270 | | |
| Pro | Leu | Leu | Ile | Met | Met | Leu | Lys | Met | Ile | Phe | Asn | Gln | Met | Ser | Val |
| | | 275 | | | | | 280 | | | | | 285 | | | |
| Glu | Gln | Cys | Lys | Thr | Gln | Met | Gly | Lys | Glu | Lys | Glu | Cys | Asn | Ser | Phe |
| | 290 | | | | | 295 | | | | | 300 | | | | |
| Leu | Ile | Ala | Val | Arg | Leu | Ala | Ser | Leu | Asn | Gln | Ile | Leu | Asp | Pro | Trp |
| 305 | | | | | 310 | | | | | 315 | | | | | 320 |
| Val | Tyr | Leu | Leu | Leu | Arg | Lys | Ile | Leu | Leu | Arg | Lys | Phe | Cys | Gln | Ile |
| | | | | 325 | | | | | 330 | | | | | 335 | |
| Arg | Asp | His | Thr | Asn | Tyr | Ala | Ser | Ser | Ser | Thr | Ser | Leu | Pro | Cys | Pro |
| | | | 340 | | | | | 345 | | | | | 350 | | |
| Gly | Ser | Ser | Ala | Leu | Met | Trp | Ser | Asp | Gln | Leu | Glu | Arg | | | |
| | | 355 | | | | | 360 | | | | | 365 | | | |

( 2 ) INFORMATION FOR SEQ ID NO:3:

( i ) SEQUENCE CHARACTERISTICS:
        ( A ) LENGTH: 1405 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

| | | | | | |
|---|---|---|---|---|---|
| GAGAGCAGAG | CCTGGGCTCC | GGCTGTCCCC | CAGTGCACTC | TGCTGCTATC | CCGCAGCTGA | 60 |
| GCCGGGAGGC | TCCGGCCCCG | TGCGCCCTAC | CGTGGCCCCG | CCACTATGGC | TAGCATGTGG | 120 |
| GCGCCGGAGC | ACTCTGCTGA | AGCGCACAGC | AACCTGTCAA | GTACTACCGA | CGACTGCGGC | 180 |
| TCCGTGTCCG | TGGCCTTTCC | CATCACCATG | ATGGTCACTG | GCTTCGTGGG | CAACGCGCTG | 240 |
| GCCATGCTGC | TCGTGTCGCG | CAGCTACCGG | CGCCGCGAGA | GCAAGCGCAA | GAAGTCTTTC | 300 |
| CTGCTGTGCA | TTGGCTGGCT | GGCGCTCACC | GACTTAGTGG | GGCAGCTCCT | GACCAGCCCG | 360 |
| GTGGTCATCC | TCGTGTACCT | GTCACAGCGA | CGCTGGGAGC | AGCTCGACCC | ATCGGGGCGT | 420 |
| CTGTGCACCT | TCTTCGGGCT | AACCATGACA | GTGTTCGGGC | TATCCTCGCT | CCTGGTGGCC | 480 |
| AGCGCCATGG | CCGTGGAGCG | CGCCCTGGCC | ATCCGTGCGC | CGCACTGGTA | TGCCAGCCAC | 540 |
| ATGAAGACTC | GCGCCACGCC | GGTACTGCTG | GGCGTGTGGC | TGTCTGTGCT | CGCCTTCGCG | 600 |
| CTGCTGCCGG | TGCTGGGCGT | GGGCCGCTAC | AGCGTGCAGT | GGCCGGGCAC | GTGGTGCTTC | 660 |
| ATCAGCACCG | GCCGGCGGG | CAACGAGACA | GACCCTGCGC | GCGAGCCGGG | CAGCGTGGCC | 720 |
| TTTGCCTCCG | CCTTCGCCTG | CTTGGGCTTG | CTGGCTCTGG | TGGTGACCTT | TGCCTGCAAC | 780 |
| CTGGCGACCA | TCAAAGCCCT | GGTGTCCCGC | TGTCGGGCCA | AAGCCGCCGT | CTCGCAGTCC | 840 |
| AGCGCCCAGT | GGGGCAGAAT | CACCACGGAG | ACGGCCATCC | AGCTCATGGG | GATCATGTGT | 900 |
| GTGCTGTCCG | TCTGTTGGTC | GCCGCTATTG | ATAATGATGT | TGAAAATGAT | CTTCAATCAG | 960 |
| ATGTCGGTTG | AGCAATGCAA | GACACAGATG | GGAAAGGAGA | AGGAGTGCAA | TTCCTTTCTA | 1020 |
| ATTGCAGTTC | GCCTGGCTTC | GCTGAACCAG | ATCTTGGATC | CCTGGGTTTA | TCTGCTGCTA | 1080 |
| AGAAAGATCC | TTCTTCGGAA | GTTCTGCCAG | ATGATGAACA | ACCTGAAGTG | GACTTTCATT | 1140 |
| GCAGTACCTG | TTTCCCTGGG | TCTGAGAATT | TCTTCTCCCA | GGGAAGGATG | ACTGAGTATT | 1200 |

```
TTGGATTGTA TCTTCTTTTG GCCTCAATTT TAAGTTTTCC TTGCCATTAA ACACACCGAG    1260

ACAAGCTTTC TTAGGATAAT CTGAGAGTCT GGTTGTTAGC TGGTTCCTGT GAAGACTGAA    1320

GACTCTGCAC TTGAGACGGG GGCAAGACGA CACAGAGCAG CATGGAGAGA CTCAGTGCAG    1380

AAATATCTCC AGCCTCAGAA CCTTT                                          1405
```

( 2 ) INFORMATION FOR SEQ ID NO:4:

( i ) SEQUENCE CHARACTERISTICS:
        ( A ) LENGTH: 361 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Met Ala Ser Met Trp Ala Pro Glu His Ser Ala Glu Ala His Ser Asn
 1               5                  10                  15

Leu Ser Ser Thr Thr Asp Asp Cys Gly Ser Val Ser Val Ala Phe Pro
            20                  25                  30

Ile Thr Met Met Val Thr Gly Phe Val Gly Asn Ala Leu Ala Met Leu
        35                  40                  45

Leu Val Ser Arg Ser Tyr Arg Arg Glu Ser Lys Arg Lys Lys Ser
    50                  55                  60

Phe Leu Leu Cys Ile Gly Trp Leu Ala Leu Thr Asp Leu Val Gly Gln
65                  70                  75                  80

Leu Leu Thr Ser Pro Val Val Ile Leu Val Tyr Leu Ser Gln Arg Arg
                85                  90                  95

Trp Glu Gln Leu Asp Pro Ser Gly Arg Leu Cys Thr Phe Phe Gly Leu
            100                 105                 110

Thr Met Thr Val Phe Gly Leu Ser Ser Leu Leu Val Ala Ser Ala Met
        115                 120                 125

Ala Val Glu Arg Ala Leu Ala Ile Arg Ala Pro His Trp Tyr Ala Ser
    130                 135                 140

His Met Lys Thr Arg Ala Thr Pro Val Leu Leu Gly Val Trp Leu Ser
145                 150                 155                 160

Val Leu Ala Phe Ala Leu Leu Pro Val Leu Gly Val Gly Arg Tyr Ser
                165                 170                 175

Val Gln Trp Pro Gly Thr Trp Cys Phe Ile Ser Thr Gly Pro Ala Gly
            180                 185                 190

Asn Glu Thr Asp Pro Ala Arg Glu Pro Gly Ser Val Ala Phe Ala Ser
        195                 200                 205

Ala Phe Ala Cys Leu Gly Leu Leu Ala Leu Val Val Thr Phe Ala Cys
    210                 215                 220

Asn Leu Ala Thr Ile Lys Ala Leu Val Ser Arg Cys Arg Ala Lys Ala
225                 230                 235                 240

Ala Val Ser Gln Ser Ser Ala Gln Trp Gly Arg Ile Thr Thr Glu Thr
                245                 250                 255

Ala Ile Gln Leu Met Gly Ile Met Cys Val Leu Ser Val Cys Trp Ser
            260                 265                 270

Pro Leu Leu Ile Met Met Leu Lys Met Ile Phe Asn Gln Met Ser Val
        275                 280                 285

Glu Gln Cys Lys Thr Gln Met Gly Lys Glu Lys Glu Cys Asn Ser Phe
    290                 295                 300

Leu Ile Ala Val Arg Leu Ala Ser Leu Asn Gln Ile Leu Asp Pro Trp
305                 310                 315                 320
```

```
            Val  Tyr  Leu  Leu  Leu  Arg  Lys  Ile  Leu  Leu  Arg  Lys  Phe  Cys  Gln  Met
                                325                      330                      335

Met  Asn  Asn  Leu  Lys  Trp  Thr  Phe  Ile  Ala  Val  Pro  Val  Ser  Leu  Gly
                                340                      345                      350

Leu  Arg  Ile  Ser  Ser  Pro  Arg  Glu  Gly
                                355                      360
```

( 2 ) INFORMATION FOR SEQ ID NO:5:

( i ) SEQUENCE CHARACTERISTICS:
        ( A ) LENGTH: 2442 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
AGCCTCTCTG  GCTTTCCAAG  CTTTTTTGAA  AGCAAGATAC  TCTGACCTCA  GTTCCGGAAA     60
GTTGGCAGCC  ACCGAGCCCC  GGTTCCGAGA  CAGCAAAAGC  TTGACAAGTT  CCGCACTGCG    120
TGGGAAGAGA  CTGATGGCTG  AGGTTGGAGG  TACCATTCCT  AGATCGAACC  GTGAGCTCCA    180
ACGCTGTGTG  TTACTAACCA  CCACCATCAT  GTCCATCCCC  GGAGTCAACG  CGTCCTTCTC    240
CTCCACTCCG  GAGAGGCTGA  ACAGCCCGGT  GACCATTCCC  GCAGTGATGT  TCATCTTCGG    300
GGTGGTGGGC  AACCTGGTGG  CCATCGTAGT  ATTGTGCAAG  TCGCGCAAGG  AGCAGAAAGA    360
GACGACCTTT  TACACTCTAG  TATGTGGGCT  GGCTGTCACT  GACCTTCTGG  GCACCTTGTT    420
GGTAAGCCCG  GTGACCATCG  CCACATACAT  GAAGGGCCAG  TGGCCCGGAG  ACCAGGCACT    480
GTGTGACTAT  AGCACCTTCA  TCCTACTTTT  CTTCGGTCTG  TCGGGTCTCA  GCATCATCTG    540
TGCCATGAGC  ATCGAGCGCT  ACCTGGCCAT  CAACCACGCC  TACTTCTACA  GCCACTACGT    600
GGACAAGCGG  CTGGCCGGCC  TCACACTCTT  CGCCATCTAT  GCATCTAACG  TGCTGTTCTG    660
CGCGCTGCCC  AACATGGGCC  TGGGCAGATC  CGAGCGGCAG  TACCCGGGCA  CCTGGTGCTT    720
CATCGACTGG  ACCACCAACG  TAACGGCCTA  CGCCGCCTTC  TCTTACATGT  ACGCCGGCTT    780
CAGCTCCTTC  CTCATCCTTG  CCACCGTGCT  CTGCAACGTG  CTGGTGTGCG  GCGCGCTGCT    840
CCGCATGCAC  CGCCAGTTCA  TGCGCCGCAC  CTCGTTGGGC  ACGGAGCAGC  ACCATGCGGC    900
TGCCGCCGCC  GCGGTAGCTT  CGGTGGCCTG  TCGGGGCCAC  GCTGGGGCCT  CCCCAGCCCT    960
GCAGCGCCTC  AGCGACTTTC  GCCGCCGCAG  GAGTTTCCGG  CGCATCGCGG  GTGCGGAGAT   1020
CCAGATGGTC  ATCTTACTCA  TCGCCACCTC  TCTGGTGGTG  CTCATCTGCT  CCATTCCGCT   1080
CGTGGTGCGA  GTGTTCATTA  ACCAGTTATA  TCAGCCAAAC  GTGGTGAAAG  ACATCAGCAG   1140
AAACCCAGAT  TTGCAGGCCA  TCAGGATTGC  TTCTGTGAAC  CCCATCCTGG  ACCCCTGGAT   1200
TTACATCCTT  CTTCGGAAGA  CTGTGCTCAG  TAAAGCCATA  GAGAAGATCA  AGTGCCTCTT   1260
CTGCCGCATT  GGCGGTTCCG  GCAGAGACAG  CTCGGCCCAG  CACTGCTCAG  AGAGTCGGAG   1320
GACATCTTCC  GCCATGTCCG  GCCACTCTCG  CTCCTTCCTC  GCCCGGGAGT  TAAAGGAGAT   1380
CAGCAGCACG  TCCCAGACCC  TCCTGTACCT  GCCAGACCTG  ACTGAAAGCA  GCCTCGGAGG   1440
CAGGAATTTG  CTTCCAGGTT  CGCATGGCAT  GGGCCTGACC  CAAGCAGACA  CCACCTCGCT   1500
GAGAACTTTG  CGAATTTCCG  AGACCTCAGA  CTCCTCCCAG  GGCCAGGACT  CTGAGAGTGT   1560
CCTGTTGGTG  GATGAGGTTA  GTGGGAGCCA  CAGAGAGGAG  CCTGCCTCTA  AAGGAAACTC   1620
TCTGCAAGTC  ACATTCCCCA  GTGAAACTCT  GAAATTATCT  GAAAAATGTA  TATAGTAGCT   1680
AAAGGGGGAA  TCTTATAAAA  TCCTGTGCAA  TAGACATACA  TAGCTGTACT  CAGAAGGGCT   1740
```

```
GTCTTCATCT GGACTCCCAC TAGAGAACAG GCGAGCTCCT GAGGGCTCTC CAAGGCTGCA      1800

GACTGAGGTC CTTGAGTGCC CAGGCTTGAA GCACATTGGC TGTCATTCTG ATGTGACTCG      1860

AGATTGCAGT TGCAACTTGG CAGCTTTTTT CTACTGGACA GGAAGATGGC AGAAGCTACG      1920

CTATTGTCAT AGCAAAAGAG CTTTCTATTT GGCACATACC AGGGGTCCAG CTACTGGAAG      1980

GGCTCTACCC CAAACTCTGA GGACTACCTT ACAGCTGACT TAAGTGTCTC ACTAAAGCAT      2040

GAAATGTGAA TTTTTATTGT TGGAAATATA ATTTAAGGTA TTTATGTTCT TCTCTGTGAG      2100

AAGGTTTATT GTTAATACAA GGTATAAAAA ACACATGATA TGCCCTCTCC TGCCAATATA      2160

ACCAGCTAAT ATTGTCGATG TTATTTTTTT TTTTCCATAA ACAAGTTCAG GCCAAAGTGT      2220

TGAAAACAGA GTGAAACTAA TATCTATAAA ATAGATATAA ATTTTTAAAA TAGTTTAGTA      2280

TCATCAAAGA AAAAATAAGT AGTATTTAAG ATGTGAAAAA TGAACAACCT AAAATATATT      2340

TTCCAAGCTA TATATAATAA TGAAAAATAA AAACATTACA TTTATTTATC CAGAAAACTG      2400

TGATTTTAGG ATTACCTAAC ATTGCTGGTA AATATTTTCA AC                         2442
```

( 2 ) INFORMATION FOR SEQ ID NO:6:

( i ) SEQUENCE CHARACTERISTICS:
        ( A ) LENGTH: 513 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Met Ala Glu Val Gly Gly Thr Ile Pro Arg Ser Asn Arg Glu Leu Gln
 1               5                  10                  15

Arg Cys Val Leu Leu Thr Thr Thr Ile Met Ser Ile Pro Gly Val Asn
            20                  25                  30

Ala Ser Phe Ser Ser Thr Pro Glu Arg Leu Asn Ser Pro Val Thr Ile
        35                  40                  45

Pro Ala Val Met Phe Ile Phe Gly Val Val Gly Asn Leu Val Ala Ile
    50                  55                  60

Val Val Leu Cys Lys Ser Arg Lys Glu Gln Lys Glu Thr Thr Phe Tyr
65                  70                  75                  80

Thr Leu Val Cys Gly Leu Ala Val Thr Asp Leu Leu Gly Thr Leu Leu
                85                  90                  95

Val Ser Pro Val Thr Ile Ala Thr Tyr Met Lys Gly Gln Trp Pro Gly
            100                 105                 110

Asp Gln Ala Leu Cys Asp Tyr Ser Thr Phe Ile Leu Leu Phe Phe Gly
        115                 120                 125

Leu Ser Gly Leu Ser Ile Ile Cys Ala Met Ser Ile Glu Arg Tyr Leu
    130                 135                 140

Ala Ile Asn His Ala Tyr Phe Tyr Ser His Tyr Val Asp Lys Arg Leu
145                 150                 155                 160

Ala Gly Leu Thr Leu Phe Ala Ile Tyr Ala Ser Asn Val Leu Phe Cys
                165                 170                 175

Ala Leu Pro Asn Met Gly Leu Gly Arg Ser Glu Arg Gln Tyr Pro Gly
            180                 185                 190

Thr Trp Cys Phe Ile Asp Trp Thr Thr Asn Val Thr Ala Tyr Ala Ala
        195                 200                 205

Phe Ser Tyr Met Tyr Ala Gly Phe Ser Ser Phe Leu Ile Leu Ala Thr
    210                 215                 220

Val Leu Cys Asn Val Leu Val Cys Gly Ala Leu Leu Arg Met His Arg
```

|     |     |     |     | 225 |     |     |     |     | 230 |     |     |     |     | 235 |     |     |     |     | 240 |
|---|---|---|---|---|---|---|---|---|---|---|---|---|---|---|---|---|---|---|---|

Gln Phe Met Arg Arg Thr Ser Leu Gly Thr Glu Gln His His Ala Ala
            245                 250             255

Ala Ala Ala Ala Val Ala Ser Val Ala Cys Arg Gly His Ala Gly Ala
            260             265             270

Ser Pro Ala Leu Gln Arg Leu Ser Asp Phe Arg Arg Arg Arg Ser Phe
        275             280             285

Arg Arg Ile Ala Gly Ala Glu Ile Gln Met Val Ile Leu Leu Ile Ala
    290                 295             300

Thr Ser Leu Val Val Leu Ile Cys Ser Ile Pro Leu Val Val Arg Val
305                 310             315                     320

Phe Ile Asn Gln Leu Tyr Gln Pro Asn Val Val Lys Asp Ile Ser Arg
            325             330             335

Asn Pro Asp Leu Gln Ala Ile Arg Ile Ala Ser Val Asn Pro Ile Leu
            340             345             350

Asp Pro Trp Ile Tyr Ile Leu Leu Arg Lys Thr Val Leu Ser Lys Ala
            355             360             365

Ile Glu Lys Ile Lys Cys Leu Phe Cys Arg Ile Gly Gly Ser Gly Arg
        370             375             380

Asp Ser Ser Ala Gln His Cys Ser Glu Ser Arg Arg Thr Ser Ser Ala
385             390             395                     400

Met Ser Gly His Ser Arg Ser Phe Leu Ala Arg Glu Leu Lys Glu Ile
            405             410             415

Ser Ser Thr Ser Gln Thr Leu Leu Tyr Leu Pro Asp Leu Thr Glu Ser
            420             425             430

Ser Leu Gly Gly Arg Asn Leu Leu Pro Gly Ser His Gly Met Gly Leu
        435             440             445

Thr Gln Ala Asp Thr Thr Ser Leu Arg Thr Leu Arg Ile Ser Glu Thr
    450             455             460

Ser Asp Ser Ser Gln Gly Gln Asp Ser Glu Ser Val Leu Leu Val Asp
465             470             475                     480

Glu Val Ser Gly Ser His Arg Glu Glu Pro Ala Ser Lys Gly Asn Ser
            485             490             495

Leu Gln Val Thr Phe Pro Ser Glu Thr Leu Lys Leu Ser Glu Lys Cys
            500             505             510

Ile